United States Patent [19]

Kopp

[11] Patent Number: 5,633,798
[45] Date of Patent: May 27, 1997

[54] METHOD AND APPARATUS FOR MEASURING OCTANE NUMBER

[75] Inventor: Vance R. Kopp, Bartlesville, Okla.

[73] Assignee: Phillips Petroleum Company, Bartlesville, Okla.

[21] Appl. No.: 423,074

[22] Filed: Apr. 13, 1995

[51] Int. Cl.$^6$ ............... G06F 19/00; G01N 33/22
[52] U.S. Cl. ............... 364/431.08; 73/35.02; 73/119 A; 123/419; 364/431.052; 364/431.061
[58] Field of Search ............... 364/431.05, 431.06, 364/431.08, 431.12, 431.04, 550.01; 73/35.01, 35.02, 119 A, 118.2, 199, 117.3, 116; 123/478, 494, 480, 488, 435, 457, 419

[56] References Cited

U.S. PATENT DOCUMENTS

| | | | |
|---|---|---|---|
| 3,557,487 | 1/1971 | Crespin et al. | 73/35 |
| 3,913,380 | 10/1975 | Jones et al. | 73/35 |
| 3,969,922 | 7/1976 | Baker et al. | 73/35 |
| 4,010,358 | 3/1977 | Morris | 235/151.35 |
| 4,276,770 | 7/1981 | Bittner | 73/35 |
| 4,331,024 | 5/1982 | Childs et al. | 73/35 |
| 4,366,701 | 1/1983 | Bittner | 73/35 |
| 4,402,212 | 9/1983 | Childs | 73/35 |
| 4,963,745 | 10/1990 | Maggard | 250/343 |
| 5,386,722 | 2/1995 | Meyer et al. | 73/117.3 |

OTHER PUBLICATIONS

ASTM D2699-92, "Standard Test Method for Knock Characteristics of Motor Fuels by the Research Method", Sep. 1992, pp. 5-18.
ASTM D2700-92, "Standard Test Method for Knock Characteristics of Motor and Aviation Fuels by the Motor Method", Nov. 1992, pp. 19-39.
"ESD Automatic Octane Rating", Electronic Systems Design, Inc. (Month, year are unknown).
"Series 8191 COMOC III, Computer Octane Comparator", Core Laboratories (month and year are unknown).
"LabCON V Improved Motor Fuel Octane Numbers", Core Laboratories, 1992. (month is unknown).
"Model 8035 LabCON V Laboratory Octane Analyzer", Core Laboratories, (month and year are unknown).

*Primary Examiner*—Kevin J. Teska
*Assistant Examiner*—Tan Nguyen
*Attorney, Agent, or Firm*—Ryan N. Cross

[57] ABSTRACT

An apparatus and method to automate octane number measurements from a knock engine is provided. A first and second reference fuel having different knock octane numbers and a test fuel having an unknown octane number are each provided to the fuel inlet of an engine at a series of flow rates. For each flow rate an average knock intensity is calculated and from the resulting series of average knock intensities, a flow rate which will give a maximum knock intensity is calculated using curve fitting techniques.

5 Claims, 6 Drawing Sheets

METHOD AND APPARATUS FOR MEASURING OCTANE NUMBER

This invention relates to a method and apparatus for determining the octane number of a fuel. In one aspect this invention relates to a computer implemented method for determining the octane number of a fuel. In another aspect, this invention relates to an apparatus which comprises an automated system for determining the octane number of a fuel.

There are many standard methods for determining the octane number of various fuels. Examples of these standard methods include ASTM Method D-2699-95 for the research method of motor fuels and ASTM Method D-2700-95 for the motor method of determining the octane number of motor and aviation fuels. To determine the octane number of a test fuel in accordance with the ASTM Methods, an ASTM-CFR engine is operated with the test fuel and with at least two reference fuels under conditions which will cause maximum knock. A pressure transducer is utilized to monitor the cylinder pressure and produce a voltage signal that is proportional to the rate of change in that pressure. A detonation meter is utilized to filter, integrate and amplify the output of the pressure transducer to produce a voltage signal that is proportional to the knock intensity. This signal is utilized to drive a knock meter which gives a scale reading relating to knock intensity. A comparison of the knock meter readings produced by the combustion of reference fuels with a knock meter reading produced by the combustion of the test fuel is utilized to estimate the octane number of the test fuel.

The ASTM methods and most other standard methods require that the engine be operated under maximum knock conditions for each fuel being provided to the engine. In the ASTM method, the air/fuel ratio that results in the maximum knock intensity is found by a successive approximations method. The fuel level in a carburetor float bowl is moved up and down and knock meter response is noted. This takes considerable fuel (at least 300–400 ml). Additionally, locating the air/fuel ratio that results in maximum knock and reading the knock meter are subjective tasks that are subject to operator error. Training an operator to locate the air/fuel ratio that results in the maximum knock intensity and to accurately read the knock meter requires a substantial investment of both time and money.

Therefore, it would be desirable to have a method and apparatus capable of determining the octane number of fuels which uses less fuel than the standard ASTM methods. Also, it would be desirable to have a method and apparatus for measuring the octane number of furl which eliminates the subjective operator error of previous methods and reduces the training costs for operators.

It is an object of this invention to develop a method and apparatus for determining the octane number of fuel which is more economical to operate in terms of the mount of fuel utilized during the determination.

It is a further object of this invention to provide a method and apparatus for determining the octane number of a fuel which eliminates the subjective operator error introduced by other methods.

SUMMARY OF THE INVENTION

In accordance with the present invention there is provided a method and apparatus for determining the octane number of a test fuel. Data characterizing a pair of reference fuels is entered into a computer. Subsequently, the computer sends a first signal to a selector valve operatively connected to the computer so that upon receiving the first signal, the selector valve changes to a first position in which the first reference fuel is introduced into a variable flow pump in fluid flow communication with an engine. The computer is also operationally connected to the variable flow pump so that it can set the flow rate at which fluid is pumped from the variable flow pump to the engine. The engine has a means for establishing a pressure signal representative of the rate of change of the cylinder pressure operationally attached to it during the combustion of the fuel. The pressure signal is sent to the computer which utilizes the signal to calculate the maximum knock level for the first reference fuel. After the maximum knock level for the first reference fuel has been determined, a second signal is sent to the selector valve. In response to the second signal, the selector valve changes to a second position to allow the second reference fuel to be introduced to the variable flow pump. Subsequently, the computer receives a pressure signal and calculates the maximum knock level for the second reference fuel. After calculating the maximum knock level for the second reference fuel, the computer sends a third signal to the selector valve. Upon receiving the third signal, the selector valve changes to a third position in which a test fuel is introduced to said variable flow pump and hence, into the engine combustion chamber. A pressure signal is sent to the computer and the computer calculates the maximum knock level for the test fuel. Upon calculating the maximum knock level for the first reference fuel, second reference fuel and test fuel, the computer calculates a test fuel octane number for the test fuel by linear interpolation using the test fuel's maximum knock level, the first reference fuel's maximum knock level and the second reference fuel's maximum knock level.

The maximum knock level for each fuel is determined by steps comprising: sending a series of flow signals to change the fluid flow rate so that each fuel is delivered for combustion within the engine at a plurality of flow rates starting at a predetermined initial flow rate and changing the flow rate towards a flow rate that is likely to produce a maximum knock intensity; sending at each flow rate a pressure signal from the engine to the computer wherein the pressure signal is representative of the rate of change of the cylinder pressure in the engine during the combustion of fuel within the engine; acquiring at each flow rate a plurality of data arrays in response to the signal wherein the plurality of data arrays contain data centered about the combustion part of the cycle of the engine; calculating an average knock intensity from the plurality of data arrays for each flow rate; comparing the average knock intensity for each flow rate, other than the initial flow rate, to the average knock intensity obtained for the previous flow rate to determine if a maximum average knock intensity for the plurality of flow rates has been found; calculating a polynomial expression for the distribution of the average knock intensity for the plurality of flow rates once a maximum average knock intensity has been found; calculating the maximum knock intensity of the polynomial expression, determining the associated flow rate; and adjusting the flow rate to the associated flow rate to obtain data arrays from which the maximum knock level for the fuel is calculated.

Additional objects and advantages of the invention will be apparent from the following detailed description of the preferred embodiments of the invention, as illustrated by the drawings in which:

DETAILED DESCRIPTION OF THE PREFERRED EMBODIMENTS

Figure 1:
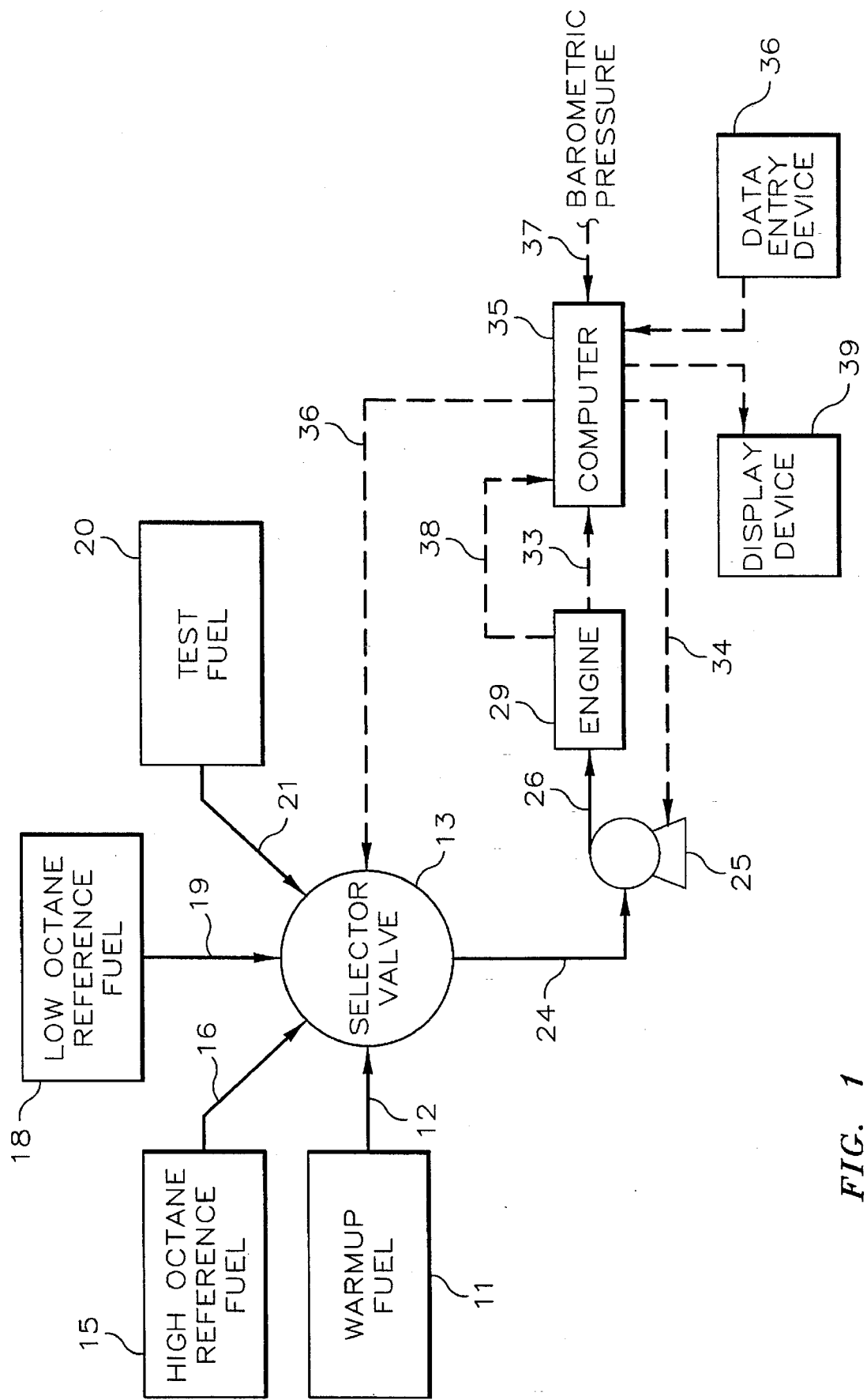
FIG. 1 is a simplified diagrammatic illustration of an apparatus for determining the octane number of a fuel in accordance with the present invention.

Referring now to the drawings and in particular to FIG. 1, a warm-up fuel is provided from the supply 11 through conduit means 12 to the selector valve 13; a high octane reference fuel is provided from the supply 15 through conduit means 16 to the selector valve 13; a low octane reference fuel is provided from the supply 18 through conduit means 19 to the selector valve 13; and a test fuel is provided from supply 20 through conduit means 21 to the selector valve 13. The supplies for the various fuels may be under pressure if desired or gravity flow may be utilized. However, due to the use of the variable flow pump as described below, it is not necessary for the various fuels to be under pressure. A particular fuel is selected through use of the selector valve 13 and is provided through conduit means 24 to the pump 25. The fuel flowing through conduit means 24 is provided from the pump 25 through conduit means 26 to the engine 29 for combustion.

A pressure transducer associated with the engine 29 monitors the cylinder pressure in the engine 29 and produces a voltage signal 33 which is proportional to the rate of change of the cylinder pressure. Signal 33 is processed by computer 35 to derive the average knock intensity for the particular fuel being provided to engine 29 at each flow rate provided by variable flow pump 25. Computer 35 is also used to control the position of selector valve 13, and, hence, which fuel passes to the engine, by voltage signal 36. Additionally, the computer sends a voltage signal 34 to control the rate at which variable flow pump 25 pumps fuel to engine 29.

Any suitable selector valve may be utilized to supply the various fuels to the engine. Preferably, the selector valve has at least three inlets, one for the high octane reference fuel, one for the low octane reference fuel and one for the test fuel. The selector valve should have one outlet which, depending on the position of the selector valve, is in fluid flow contact with the high octane reference fuel, the low octane reference fuel, or the test fuel. As shown in FIG. 1, the selector valve has four inlets, with the fourth inlet being in fluid flow contact with the warm-up fuel and, hence, the selector valve has a fourth position wherein the outlet is in fluid flow contact with the warm-up fuel. Additionally, in place of the warm-up fuel, or in addition to the four fuels in fluid flow contact with the selector valve in FIG. 1, a second test fuel could be in fluid flow contact with selector valve 13 in the same manner as the other fuels and, hence, the system could determine the octane numbers of both test fuels.

Figure 2:
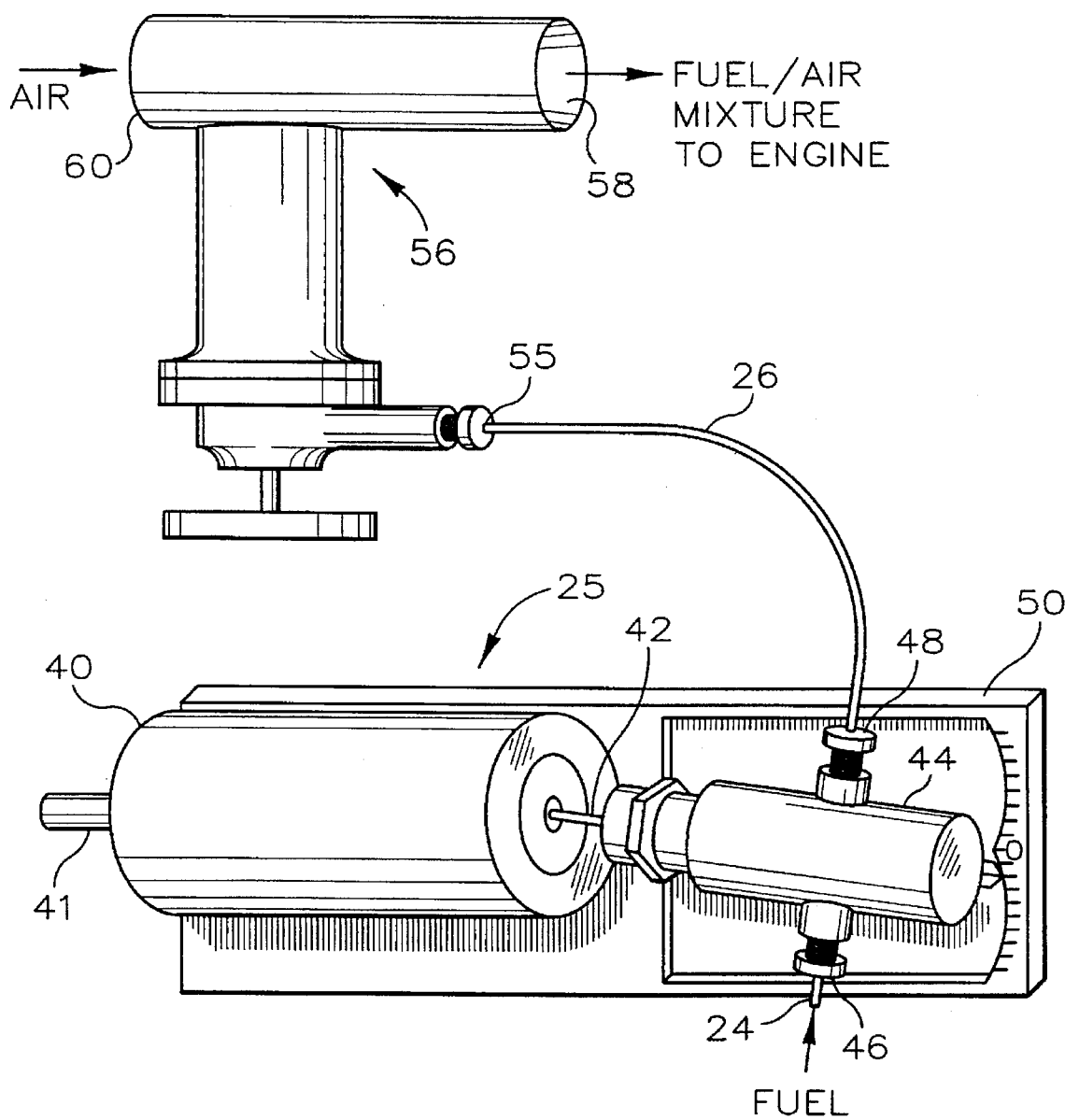
FIG. 2 is an illustration of a suitable variable flow pump and fuel inlet system for the apparatus illustrated in FIG. 1.

A suitable timed variable flow pump 25 is illustrated in FIG. 2. In FIG. 2, variable flow pump 25 is illustrated as a valveless pump, such as those manufactured by Fluid Metering, Inc., Oyster Bay, N.Y. The pump comprises bearing unit 40, piston 42, cylinder 44, inlet port 46, outlet 48 and swivel means 50. Bearing unit 40 is powered by engine 29. The bearing unit 40 and engine 29 are coupled so as to accommodate precise fuel volume delivery and timing. The fuel delivery is timed to the intake stroke of engine 29 by a half speed (one half engine speed) shaft 41. Bearing trait 40 is capable of synchronously rotating and reciprocating piston 42. A duct on the piston connects the input and output ports alternately with a pumping chamber contained within cylinder 44, i.e., one port on the pressure portion of the pumping cycle and the other on the suction cycle. This design for the pump gives a minimum of dead volume due to the configuration of the piston and pumping chamber.

The cylinder 44 is mounted onto swivel means 50 in a manner such that swivel means 50 can be adjusted to change the angle at which piston 42 meets bearing unit 40. Additionally, piston 42 is connected to bearing unit 40 so as to allow the angle to be changed. The angle at which piston 42 meets bearing unit 40 controls the stroke length of piston 42 so as to control the flow rate, and hence, the fuel volume delivery.

Thus, to change the flow rate of the fuel, computer 35 sends a signal to swivel means 50. In response to this signal, swivel means 50 increases or decreases the angle at which piston 42 meets bearing unit 40 and thereby changes the flow rate.

Fluid entering port 46 from the selector valve via conduit 24 is pumped through to port 48 at the selected flow rate and enters conduit 26. Fuel flowing through conduit 26 enters fuel inlet system 56 through port 55. Fuel inlet system 56 is connected at outlet 58 to engine 29 and is connected to an air intake line at inlet 60.

Figure 3:
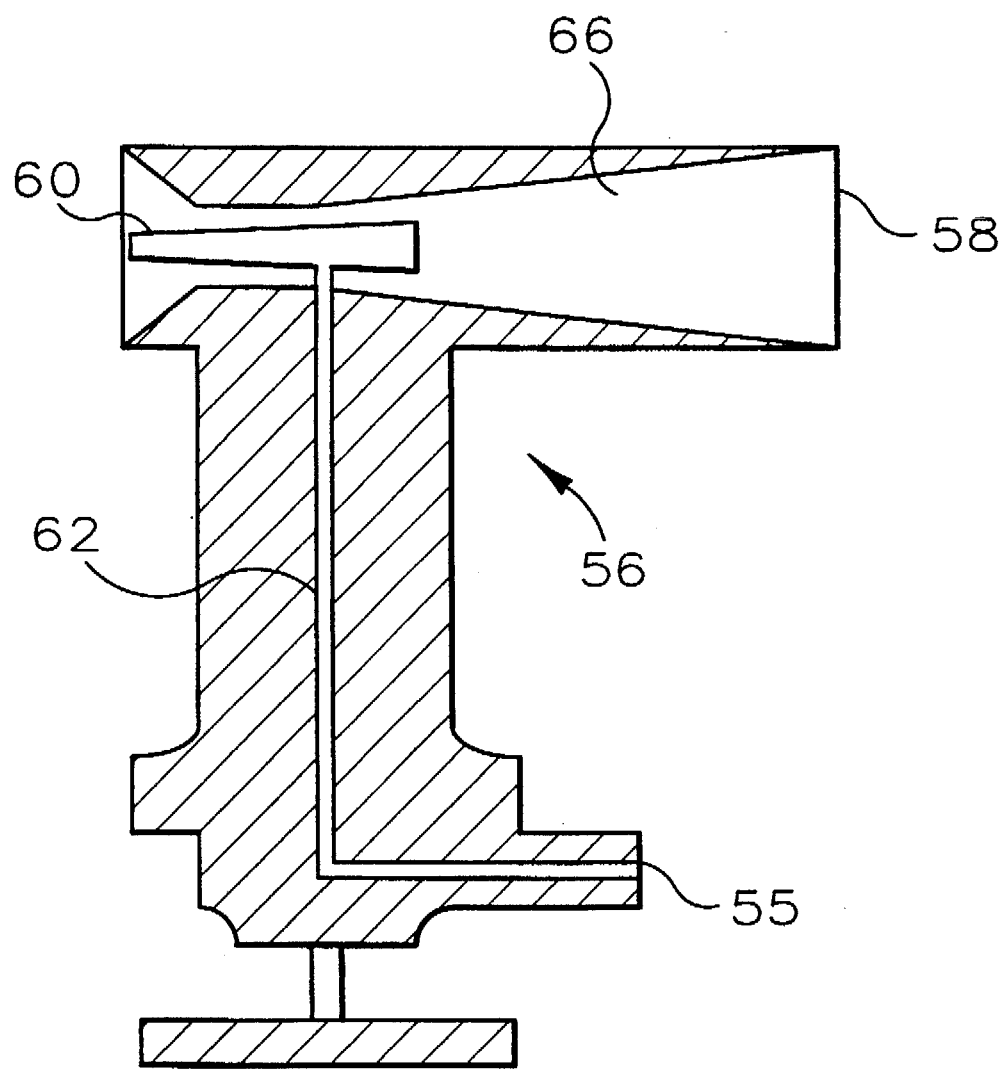
FIG. 3 is a cutaway view of the fuel inlet system illustrated in FIG. 2.

Fuel inlet system 56 can be better seen from FIG. 3. Fuel entering port 55 flows upward through conduit 62 and enters venturi tube 64. Air entering chamber 66 through inlet 60 at a constant rate and flows through venturi tube 64 and mixes with fuel therein. Subsequently the air/fuel mixture exits chamber 66 through outlet 58 and is introduced into engine 29 for combustion.

Pump 25 along with fuel inlet system 56 provides for a system capable of precise control of the air/fuel mixture. A valveless pump, such as those manufactured by Fluid Metering, Inc., has volume reproducibility of about 0.1% between stroke cycles. By changing the angle at which the piston 42 meets bearing unit 40, the flow rate of the fuel is changed and, hence, the ratio of air to fuel in the air/fuel mixture produced by the fuel inlet system. The use of the valveless pump illustrated provides for precise control of the pumping rate by allowing small changes in the angle at which piston 42 meets motor 40 and, hence, small changes in the pumping rate.

Any suitable engine may be utilized for the octane number determination. The engine 29 is preferably the ASTM-CFR engine which is required in the standard ASTM method for determining octane number. The ASTM-CFR engine is a one-cylinder, four cycle engine which conforms to the requirements of ASTM standard D-2699-95 and also includes a D1 pressure transducer. Other engines may be required by other standard tests.

Returning now to FIG. 1, in operation, the warm-up fuel flowing from the supply 11 is utilized to warm-up engine 29 and may be utilized for any calibrations required. One of the reference fuels can be used for warm-up purposes, if desired, or natural gas may be used. If natural gas is used to warm up the engine, it is preferable that it be delivered directly to the engine inlet and not flow through selector valve 13 or variable flow pump 25.

Information regarding the reference fuels, such as their octane number is entered into the computer through an appropriate data entry device 36. Computer 35 is in communication with an appropriate barometer and thus automatically receives information on the barometric pressure through signal 37. Additionally, the computer receives information on engine temperature(s) through signal 38. After the engine has been warmed up, the computer calculates the appropriate compression ratio using the information on the reference fuels, barometric pressure, and engine temperature. The initial pump settings are entered by the operator or can be estimated by the computer. The high octane reference fuel, low octane reference fuel and test fuel are then provided sequentially to the engine 29. The high octane reference fuel, low octane reference fuel and test fuel may be provided to the engine 29 in any order, but preferably, the high octane reference fuel is provided to the engine 29, then the low octane reference fuel and then the test fuel.

For most purposes, a four octane number spread between the reference fuels can be used. Some of the most generally used sets of reference fuels are 80/84, 84/88, 90/94, 94/98 and 96/100. The 90/94 pair of reference fuels is most often used when testing fuels under ASTM Method D-2699-95 and the 80/84 and 84/88 pairs of reference fuels are most often used when testing fuels under ASTM Method D-2700-95. For estimating the octane the reference fuels do not have to bracket the test fuels, for example: the 90/94 pair of reference fuels can be used to rate test fuels in the range of about 88 to about 95 octane, and the 96/100 pair of reference fuels can be used to rate test fuels in the range of about 95 to about 100 octane. However, in order to conform to the ASTM methods and to obtain more accurate results the reference fuels should bracket the test fuels and therefore such bracketing is preferable, for example: it is preferable that the 94/98 pair of reference fuels be used to rate test fuels in the range of 94 to 98 octane. Preferably, the high octane reference fuel and the low octane reference fuel should conform to the fuel requirements of ASTM Method D-2699-95 and D-2700-95 if the research octane number or motor fuel octane number of a gasoline is being determined.

Each fuel is delivered to the engine in a series of differing flow rates by variable flow pump 25. A fuel is first delivered to engine 29 at a predetermined initial flow rate which is known to be either higher or lower than the flow rate that will produce the maximum knock level for that fuel. Subsequently, the fuels are delivered to the engine at sequentially decreasing or increasing flow rates, respectively. Although an initial flow rate that is either higher or lower than the maximum knock level can be utilized, it is preferred to use the initial flow rate that is lower than the maximum knock level flow rate and, therefore, the invention will be described in terms of choosing the lower initial flow rate. However, it should be understood that either the lower or higher initial flow rate may be used.

Fuel delivered to engine 29 is combusted and the pressure transducer in engine 29 sends signal 33, which is representative of the rate of change of the engine cylinder pressure, to computer 35 where the signal is utilized to derive an average knock intensity for the fuel at a particular flow rate as further described hereinafter. After the computer has received sufficient data to calculate the average knock intensity of the fuel at a flow rate, it sends a signal 34 to variable pump 25 which results in an increase in the fuel flow rate. At the increased flow rate the computer will once again receive a signal 33 and determine an average knock intensity.

After average knock intensity is determined, the computer determines whether one of the flow rates has resulted in a maximum average knock intensity when compared to the average knock intensities at the other flow rates. After a maximum average knock intensity for the tested flow rates has been found, the computer calculates a fluid flow rate based on the measured knock intensity distribution for all flow rates that will give the maximum knock intensity, or maximum knock level, resets the pump to that flow rate and receives a data array for knock at that flow rate from which it calculates the maximum knock level for the fluid. The computer displays the knock values for each flow rate and the resulting maximum knock level on display device 39, which can be a video terminal. After the maximum knock level has been calculated, the computer sends a signal 36 to selector valve 13. In response to signal 36, selector valve 13 changes to a different position and, accordingly, introduces one of the other fuels to pump 25 for delivery to engine 29. Thus, sequentially, selector valve 13 is set to deliver first the high octane reference fuel, then the low octane reference fuel, and finally the test fuel to pump 25 and, hence, the engine 29. Typically, no more than about 50 ml of each fuel will be required to find the maximum knock level of each fuel.

After the octane number of the test fuel has been determined, the computer can be programmed to recalculate the initial pump settings using the information obtained to refine the initial pump setting and, subsequently, repeat the process for determining the test fuel octane number. While not necessary, this second determination of the test fuel octane number can result in a more accurate value.

Figure 4:
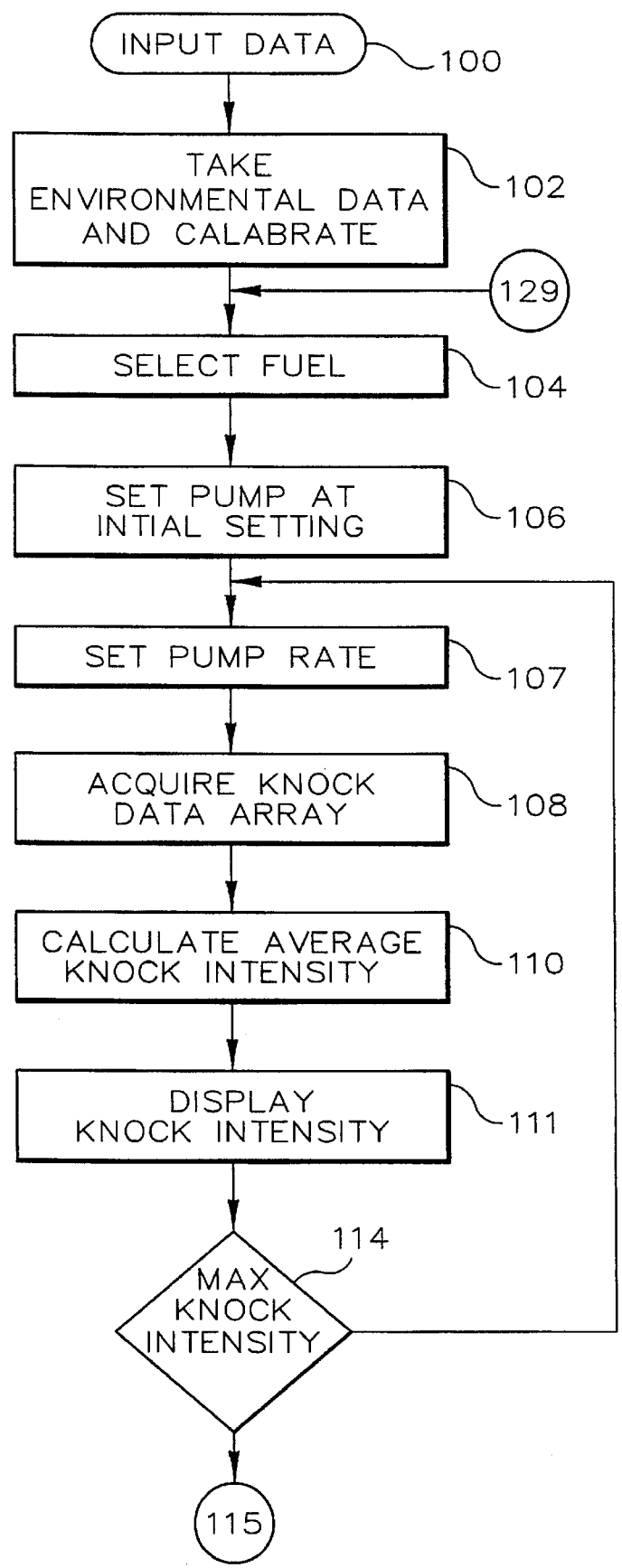
FIGS. 4 and 5 are a flow chart illustrating the preferred method for determining the octane number of a fuel in accordance with the present invention.
Figure 5:
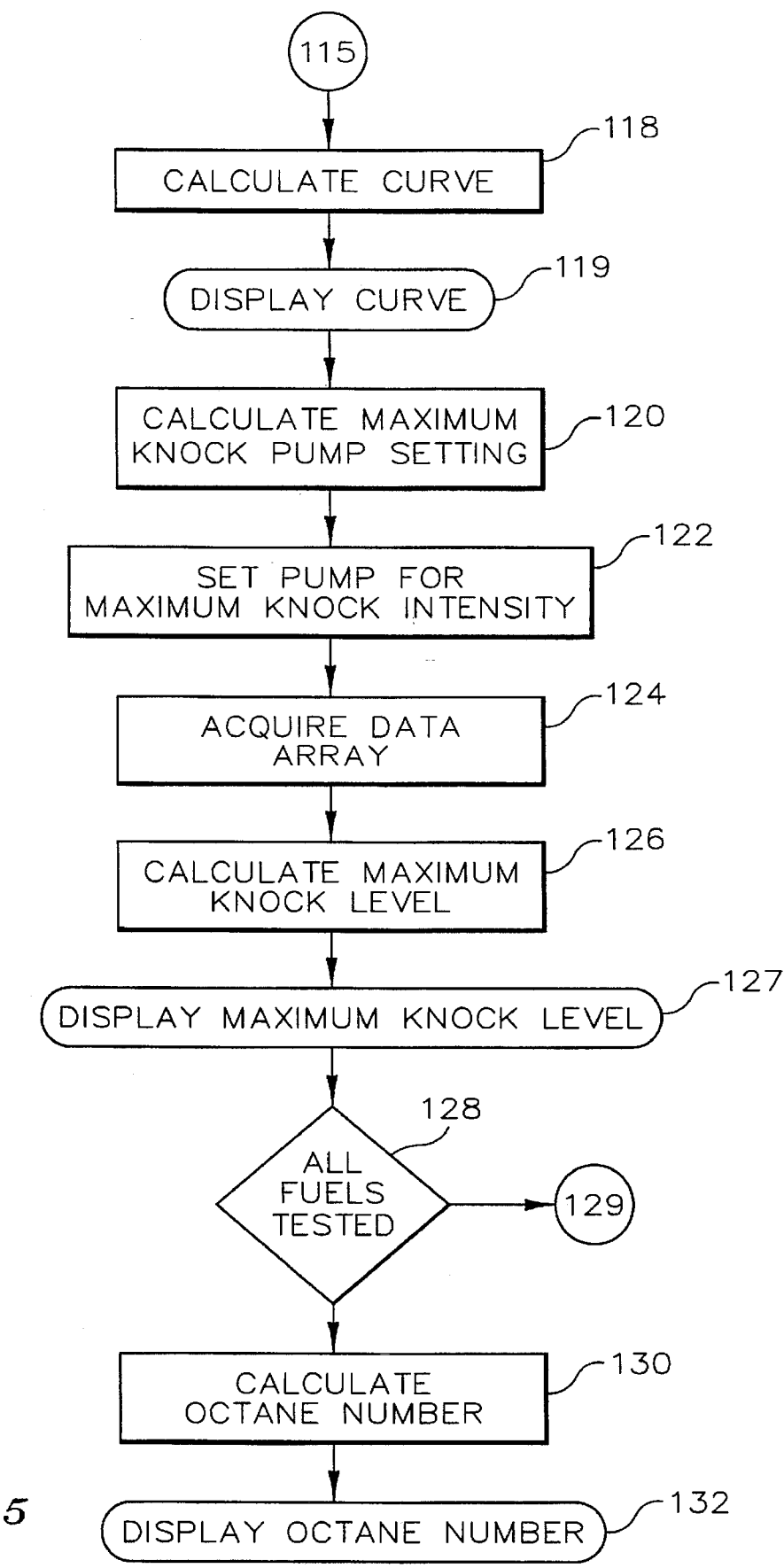

Referring now to FIGS. 4 and 5, there is illustrated a flow chart of the method of the present invention used to determine the octane number of the test fuel. In a first step, data is entered regarding the reference octanes, and the sample descriptions and environmental data is taken to determine barometric pressure and the engine temperature. This information is used to calculate the initial pump settings and calibrate the model in step 102. After calibration, the first fuel is selected in step 104, typically the high octane reference fuel. This is accomplished by sending the appropriate signal 36 to selector valve 13. In step 106 the computer sets the variable flow pump to the initial flow rate by sending an appropriate signal 34 to variable flow pump 25. If the average knock intensity for the initial flow rate has not been calculated, then the computer proceeds to step 108. If it has been calculated, the computer sends the appropriate signal 34 to pump 25 to increase the timed variable flow pump settings so that the fuel flow rate is increased in step 107 and then proceeds to step 108. Once the variable flow pump has been set so that the fuel is entering the engine at the appropriate flow rate, the computer, in step 108, acquires an array of data on the knock intensity in response to signal 33 from the pressure transducer in engine 29, as illustrated in FIG. 2. Using the data array obtained in step 108, the computer in step 110 calculates an average knock intensity for the fuel at the present flow rate. The computer calculates the average knock intensity by averaging the knock result of a plurality of combustion events in the engine cylinder. Generally, twenty or more combustion events are average, typically about 32 combustion events. After an average knock intensity is obtained and the average knock intensity is displayed in step 111, the computer moves to step 114 where it determines whether it has found a maximum average knock among the average knock values it has obtained.

Figure 6:
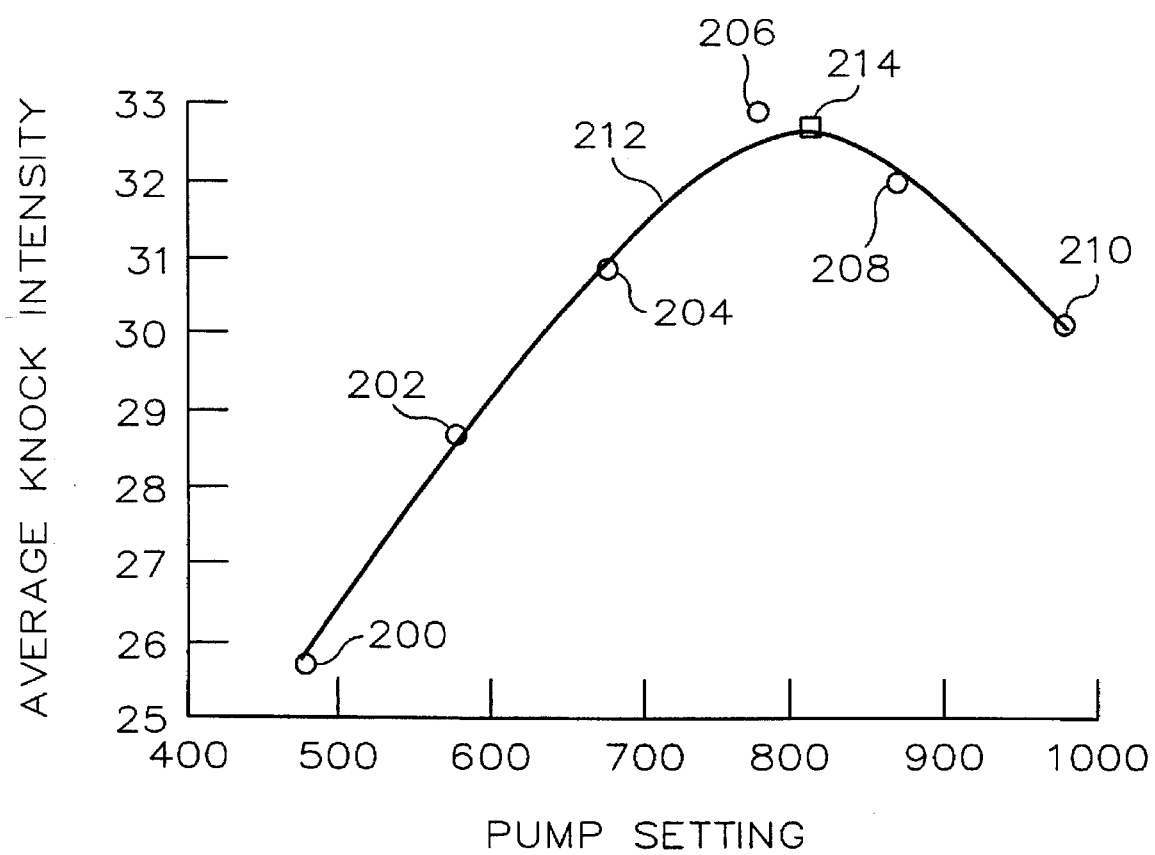
FIG. 6 is a graphical illustration of the average knock intensities at various pump settings for a test fuel.

Turning now to FIG. 6, a graphical illustration of the average knock intensities is shown. FIG. 6 is a plot of average knock intensity versus the fuel pump setting. Both the average knock intensity and the fuel pump setting are on arbitrarily chosen scales to represent digitally the analog signal received from the pressure transducer and the signal sent to the fuel pump to control the fuel pump rate. The computer first calculates average knock intensity for the initial flow rate 200. It then calculates average knock intensity values 202, 204, 206, 208 and 210. After each average knock intensity value 202, 204, 206, 208 and 210, the computer compares with the previous knock intensity value obtained to determine if the previous average knock intensity is greater or less than the newest average knock intensity. Upon finding that the average knock intensities are decreasing rather than increasing, the computer determines that it has found a maximum average knock intensity. Preferably, the program will determine that a maximum average knock intensity has been obtained by comparing the present average knock intensity with the largest prior average knock intensity until the present average knock intensity has decreased from the largest prior average knock intensity by a predetermined amount. Thus, value 206 represents the greatest average knock intensity obtained. Upon obtaining value 208 the computer compares value 208 with value 206. If the decrease in knock intensity between values 208 and 206 is not greater than the predetermined mount then a new value 210 is obtained. If the decrease between values 206 and 210 is greater than the predetermined amount then the computer continues on to step 118 in FIG. 5.

Referring now back to FIGS. 4 and 5, if the computer has not found a maximum average knock intensity value, then it returns to step 108 to acquire another data array for a higher pumping rate. If in step 114 a maximum average knock intensity has been found, then the computer proceeds to step 118 to calculate an equation for a curve that fits the average knock intensity points obtained when the average knock intensity is plotted versus fuel flow rate. The computer will calculate the curve using an appropriate least squares method to calculate a third order polynomial expression for the curve. In order to insure an accurate curve fit, it is desirable that at least three average knock intensity points are obtained prior to the maximum average knock intensity. After calculating the third order polynomial expression for a curve fitting the average knock intensity values, the computer will display the curve in step 119 and then continue on to step 120 where it will calculate the maximum of the curve and use this maximum to determine a flow rate for the fuel that would result in a maximum knock intensity ("maximum knock level"). The calculation of the maximum knock level can be better understood with reference to FIG. 6. In the graphical illustration, curve 212 represents the third order polynomial expression for the average knock values obtained. By taking the derivative of this polynomial expression, the computer can calculate value 214. From value 214 the computer can obtain the corresponding pump setting or fuel flow rate that will produce the maximum level.

Having calculated the flow rate that will result in the maximum knock level, the computer resets the variable flow pump to that flow rate in step 122 and once again acquires a data array in response to a signal from the pressure transducer in engine 29 in step 124. From this data array the maximum knock level for the fuel is calculated in step 126 and then is displayed on an appropriate display device in step 127. The computer then moves on to step 128 and determines whether all fuels have been tested. If they have not been, the computer returns to step 104 to select the next fuel. When the high octane reference fuel, low octane reference fuel and test fuel have all been tested the computer calculates the octane number for the test fuel in step 130. Since the octane number of the high octane reference fuel and low octane reference fuel are known and the maximum knock levels have been found for both reference fuels and the test fuel, the octane number of the test fuel can be derived directly by comparing the maximum knock level of the test fuel to the maximum knock levels of the high octane reference fuels and the low octane reference fuel and using linear interpolation. After calculating the octane number in step 130, the computer displays the octane number in step 132 at an appropriate video terminal or by printing out a hard copy. Additionally, the computer can be set to display the average knock intensity versus flow rate graph as illustrated in FIG. 6 as well as other data, such as the engine temperature, the barometric pressure and the octane numbers of the reference fuels.

Many different types of software programs could be written in different languages and formats which would allow a suitable computer to carry out its required functions. While many different software programs could be developed to accomplish the required functions, a suitable software program written for Lab Windows for DOS using the C programming language and NI-DAC®, marketed by National Instruments Corporation, Austin, Tex., is attached as Appendix I to the present application.

The invention has been described with particular reference to the standard ASTM methods for determining the octane number of gasoline. The ASTM methods require the use of the ASTM-CFR engine. It is again noted that the present invention is applicable to all octane measurement using any suitable engine.

The invention has been described broadly in terms of the present preferred embodiment. Reasonable variations and modifications are possible by those skilled in the art within the scope of the described invention and the appended claims.

Appendix I

Page 1    LG3M.C    Thu Apr 13 05:57:25 1995

```
1    /*   KEAS w/ LW 2.3 & NIDAQ 4.4.1 & MS C 7.00 */
2    /* rev 1.3 January 15, 1992    pak      */
3    /* rev 1.4 April 1, 1992       njf      */
4    /* rev 1.5 October 28, 1992    jlf      */
5    /* rev 1.6 March 21, 1994      vrk      */
6    /* while counter on DAQ for min KI, leaded fuels delays  */
7    /* moving average on max knock, no temp on maxnok */
8    /* oh hour timer over-double, UIR Changes config,ldat*/
9    /* revise maxnok routine and graphing */
10   /* include head set indicator, baro and cntr corr. */
11   /* timer and end of run indicator */
12
13   #include "C:\LW\include\lwsystem.h"
14   #include "C:\LW\include\formatio.h"
15   #include "C:\LW\include\userint.h"
16   #include "C:\LW\include\analysis.h"
17   #include "C:\LW\include\dataacq.h"
18   #include "C:\LW\INCLUDE\utility.h"
19   #include "C:\LW\INCLUDE\rs232.h"
20
21   #include "lmain.h"
22   #include "ldatm.h"
23   #include "lconfig.h"
24   #include "labort.h"
25   #include "ltemp.h"
26   #include "cnfg.h"
27   #include "lerr.h"
28   #include "lfinala.h"
29   #include "lfinalia.h"
30   #include "lhelp.h"
31   #include "lhelp2.h"
32   #include "lhelp3.h"
33   #include "lhelp4.h"
34
35   #define  TRUE   1
36   #define  FALSE  0
37   #define PORTA 1                          /* serial port for Z-World */
38   #define PORTB 4                          /* serial port for RS-422 */
39
40   void runsson ( void );
41   void confg ( void );
42   void maxknock ( double *, int *, double *, int);
43   void valve ( int );
44   void setpump (double);
45   void sample ( double *, int);
46   void update ();
47   void abort_check ( int *handle, int *id );
48   void temp_read (int);
49   void log_faults (int, char[80]);
50   void final_data ( int, int, double, double, char[4], int, char[3], double)
     ;
51   void help_read (int);
52   void data_reset (int);
53   void err_routine (char*, int);
54   void head_set ( void );
55   void gas_valve (int);
56   void drain_valve (char[2], int);
57   void rs_comm (int, char[4]);
58   void wait (double);
59
```

Page 2    LG3M.C Thu Apr    05:57:25 1995

```
60   int panel[13], abort_flag, cur_fit, stat_flag, sample_index;
61   int test_type, fuel, error, id, handle, w_u, cnt_1, hd_cor;
62   static double ref_pump_set, octane[6], max_knock[5], baro;
63   static double max_knock_pump[5], initial_guess, st_time, up_pump;
64   static double mxknk_1[10], mxknk_2[10], mxknk_3[10], mxknk_4[10], mxpmp_1[
     10],
65   mxpmp_2[10], mxpmp_3[10], mxpmp_4[10], oct_3[10], oct_4[10];
66   char desc1[10], oper[6], path[80], desc2[10], up_ld[25];
67   static int circ_dat[501], sect_dat[251], text_valy, text_valg;
68   static double maxnok_dat[129], y_doubl[251];
69
70
71   void main()
72   {
73     int board;
74
75     panel[0] = LoadPanel ("lmain.uir", MAIN);  /* load panels for program */
76     panel[1] = LoadPanel ("ltemp.uir", TEMP);
77     panel[2] = LoadPanel ("lconfig.uir", CONFIG);
78     panel[3] = LoadPanel ("ldatm.uir", DATA);
79     panel[4] = LoadPanel ("labort.uir", ABORT);
80     panel[5] = LoadPanel ("cnfg.uir",CNFG);
81     panel[6] = LoadPanel ("lerr.uir",ERROR);
82     panel[7] = LoadPanel ("lfinala.uir",FINAL);
83     panel[8] = LoadPanel ("lhelp.uir",HELP);
84     panel[9] = LoadPanel ("lhelp2.uir",HELP);
85     panel[10] = LoadPanel ("lhelp3.uir",HELP);
86     panel[11] = LoadPanel ("lhelp4.uir",HELP);
87     panel[12] = LoadPanel ("lfinal1a.uir",FINAL);
88
89     /* check to see that all panels are loaded OK */
90     if ( (panel[0] < 0) || (panel[1] < 0) || (panel[2] < 0) ||
91          (panel[3] < 0) || (panel[4] < 0) || (panel[5] < 0)
92          || (panel[6] < 0) || (panel[7] < 0) || (panel[8] < 0)
93          ||(panel[9] < 0) || (panel[10] < 0) || (panel[11] < 0)
94          || (panel[12] < 0))
95        err_routine ("Load Panel", -99);      /* quit if panels don't load */
96
97                /* read config in from file */
98   /*error = OpenFile ("c:\\keas\\help\\portcnfg.txt", 1,0,1);*/
99       /*ScanFile (error,"*/
100
101                         /* configure I/O boards */
102    error = Init_DA_Brds (1, &board);
103    if ( error != 0 )
104      err_routine ( "Init_DA_Brds", error );
105    error = AI_Configure (1, -1, 0, 10, 0, 0);
106    if ( error != 0 )
107      err_routine ( "AI_Config", error );
108    error = Set_DAQ_Mode (1, 0);
109    error = DAQ_Config (1, 0, 0);              /* config A/D for interupts */
110    up_pump = 0.0;
111    rs_comm (PORTB, "Kz");                    /* get initial pump position */
112    Scan(up_ld,"%s)%f[p0]",&up_pump);
113    abort_flag = FALSE;                                /* set abort flag */
114    st_time = Timer();
115    RecallPanelState (panel[5], "c:\\keas\\pnl\\cnfgm.pnl"); /* recall last*
     /
116    GetCtrlVal (panel[5], CNFG_W_U, &w_u);              /* settings */
117    GetCtrlVal (panel[5], CNFG_REFPUMP, &ref_pump_set);
```

Page 3    LG3M.C  Thu Apr `  05:57:25 1995

```
118        gas_valve(TRUE);                              /* sense gas valve */
119        valve ( w_u );                           /* set valve to warm up fuel */
120        DisplayPanel(panel[0]);                       /* show main menu */
121        SetActiveCtrl (MAIN_CONFIG);
122        while (TRUE) {                           /* main menu infinite loop */
123          GetUserEvent(TRUE, &handle, &id);           /* check for user input */
124          switch (id) {
125            case MAIN_SSON:                           /* do test */
126              HidePanel (panel[0]);
127              runsson ();
128              DisplayPanel(panel[0]);
129              break;
130            case MAIN_CONFIG:        /* change test configuration settings */
131              HidePanel (panel[0]);
132              confg ();
133              DisplayPanel(panel[0]);
134              break;
135            case MAIN_EXIT:                           /* outa here!! */
136              DAQ_Clear (1);
137              setpump (0.0);
138              exit (0);                               /* normal exit */
139              break;
140            default:
141              break;
142            case MAIN_HELP:                           /* online help */
143              InstallPopup (panel[11]);
144              help_read (panel[11]);
145              RemovePopup (0);
146              break;
147          }
148        }
149      }                                               /* end of main */
150      void runsson ( void )
151      {
152        char *meth_nam, desc_old[10], desc_old2[10],
153        tol[10], num_dat[80], engno[3], *drve, tmp[150], filen[13];
154        int fuel_num, pump_set_est[5], offset_pump, fuel_offset, replic, z,
155        ordr_rn, file, prt, i, j, k, rep, samp, pump_val, adj_offset;
156        int cnt, orde, pnl, ad_baro, baro_avg, err;
157        double initial_guess, diff2, diff1, slope;
158        double rate, itemp, mtemp, over, end_time;
159        double std, tol_std[4], baro_rd, std_temp, tsf, tsf1;
160
161        meth_nam = "     "; drve = "        ";
162        data_reset (1);                               /* reset data summary arrays */
163        data_reset (2);
164        replic = 0;                                    /* reset replicate counter */
165        k = 0;                                         /* reset data setup counter */
166
167        while (TRUE) {
168        if (k == 0) {             /* reset variables if reconfig or new test */
169          GetCtrlVal (panel[2], CONFIG_TEST, &test_type);
170            if (test_type == 1)
171              meth_nam = "RON";
172            else
173              meth_nam = "MON";
174          SetCtrlVal (panel[3], DATA_ENGINE, meth_nam);
175          baro_avg = 0;
176          baro_rd = 0;
177          for (i=1;i<=10;i++)    {                    /* read baro and calibr. */
```

Page 4    LG3M.C  Thu Apr    05:57:25 1995

```
178
179            AI_Read(1,2,1,&ad_baro);
180              baro_avg += ad_baro;
181          }
182        baro_avg = baro_avg/10;
183        baro = (( baro_avg/409.6*1.54) + 23.6);
184        SetCtrlVal (panel[3], DATA_BARO_1, baro);
185        GetCtrlVal (panel[3], DATA_BARO_1, &baro);
186        Fmt ( filen, "%s(baro.%s", meth_nam);/* get info for baro corrctns */
187          MakePathname ("c:\\keas", filen, path);
188          file = OpenFile (path, 1, 2, 1);
189          while (k <= 101 && baro_rd != baro)  {       /* and file pointer */
190            ReadLine (file, tmp, 16);
191            Scan (tmp, "%s)%f[x]%i[x]%f[x]", &baro_rd, &hd_cor, &std_temp);
192            k++;
193          }
194          SetFilePtr (file, 0, 0);
195          CloseFile (file);
196        SetCtrlVal (panel[3], DATA_STTEMP, std_temp);
197        temp_read (0);    /* get temperature readings 0 - test not running */
198        GetCtrlVal (panel[2], CONFIG_FUEL, &fuel);     /* get test config */
199        GetCtrlVal (panel[2], CONFIG_OPER, oper);                /* operator */
200        SetCtrlVal (panel[3], DATA_OPERT, oper);
201        SetCtrlVal (panel[3], DATA_DATE, datestr());
202        GetCtrlVal (panel[2], CONFIG_NOSAMP, &samp);   /* no samples 1 or 2 */
203        /* run order 1 = green fuel first 0 = yellow fuel first */
204        GetCtrlVal (panel[2], CONFIG_ORD_1, &ordr_rn);/* run order  samples */
205        GetCtrlVal (panel[2], CONFIG_OH, &over);                /* hrs since OH */
206        if (over > 0.0)
207          SetCtrlAttribute (panel[2], CONFIG_OH, 15, 0);
208        if (samp == 3 && ordr_rn == 1){             /* disable data buttons */
209          SetCtrlAttribute (panel[3], DATA_YLW, 15, 0);
210          SetCtrlAttribute (panel[3], DATA_DESC1, 15, 0);
211          SetCtrlAttribute (panel[3], DATA_DESC3, 15, 0);
212          SetCtrlAttribute (panel[3], DATA_GUESS3, 15, 0);
213        }                                             /* based on samp no and */
214        if (samp == 3 && ordr_rn == 0)  {              /* run order */
215          SetCtrlAttribute (panel[3], DATA_GRN, 15, 0);
216          SetCtrlAttribute (panel[3], DATA_DESC2, 15, 0);
217          SetCtrlAttribute (panel[3], DATA_DESC4, 15, 0);
218          SetCtrlAttribute (panel[3], DATA_GUESS4, 15, 0);
219        }
220
221        GetCtrlVal (panel[2], CONFIG_NOREP, &rep);     /* no of replicates */
222        GetCtrlVal (panel[2], CONFIG_PRINT, &prt);              /* auto print */
223        SetCtrlVal (panel[3], DATA_NOREP, rep);        /* set no of reps */
224      k++;                                   /* increment setup counter */
225      DisplayPanel (panel[3]);
226    }
227    SetCtrlVal (panel[3], DATA_OVER, over + ((timer() - st_time)/3600.0));
228    SetCtrlVal (panel[3], DATA_TIME, timestr());
229    head_set();                       /* indicate corrected head settings */
230    GetUserEvent(FALSE,&handle,&id);            /* check for user input */
231    switch (id) {
232      case DATA_RUN:                            /* set up and run test */
233        GetCtrlVal (panel[3], DATA_DESC1, desc1);
234        GetCtrlVal (panel[3], DATA_DESC2, desc2);
235        error = CompareStrings (desc1, 0, desc_old, 0, 1);
236        if (error != 0) { /* incr counter if sample desc is the same */
237          data_reset (1);                      /* reset data smumary array */
```

Page 5    LG3M.C    Thu Apr 05:57:25 1995

```
238                DefaultPanel (panel[7]);        /* clear data summary screen */
239                text_valy = FINAL_TEXT_1; /* reset txt value for data summ */
240                replic = 0;                     /* reset replicate loop counter */
241             }
242             error = CompareStrings (desc2, 0, desc_old2, 0, 1);
243             if (error != 0) { /* incr counter if sample desc is the same */
244                data_reset (2);                 /* reset data smumary array */
245                DefaultPanel (panel[12]);       /* clear data summary screen */
246                text_valg = FINAL_TEXT_1; /* reset txt value for data summ */
247                replic = 0;                     /* reset replicate loop counter */
248             }
249             if (abort_flag == FALSE)
250                replic = 0;                     /* reset replicates, if no abort */
251             SetCtrlAttribute (panel[3], DATA_DESC1, 10, 0);
252             SetCtrlAttribute (panel[3], DATA_DESC2, 10, 0);
253             SetCtrlAttribute (panel[3], DATA_GRN, 16, 1);
254             SetCtrlAttribute (panel[3], DATA_RUN, 16, 1); /* hide push butto
     ns */
255             SetCtrlAttribute (panel[3], DATA_HELPR_1, 16, 1);
256             SetCtrlAttribute (panel[3], DATA_YLW, 16, 1);
257             SetCtrlAttribute (panel[3], DATA_RETURN, 16, 1);
258             SetCtrlAttribute (panel[3], DATA_TEMPR, 16, 1);
259             SetCtrlAttribute (panel[3], DATA_CONFG, 16, 1);
260             SetCtrlAttribute (panel[3], DATA_OCTANE3, 4, 14);
261             SetCtrlAttribute (panel[3], DATA_OCTANE4, 4, 10);
262             SetCtrlVal (panel[4], ABORT_TEST, "TEST IN PROGRESS");
263             SetActivePanel (panel[4]);          /* move cursor to panel 4 */
264             GetCtrlVal (panel[5],CNFG_POFFSET, &offset_pump);  /*PRF's offs
     et */
265             GetCtrlVal (panel[5],CNFG_FOFFSET, &fuel_offset);  /*sample off
     set*/
266             /*if (fuel == 1)  {*/             /* if leaded increase offset */
267                /*offset_pump = 1.3*offset_pump;*/
268                /*fuel_offset = 1.3*fuel_offset;  */
269             /*}*/
270             GetCtrlVal (panel[3], DATA_ITEMP, &itemp);
271             GetCtrlVal (panel[3], DATA_MTEMP, &mtemp);
272
273          for ( z = replic+1; z <= rep; z++){
274             abort_flag = FALSE;                 /* init abort_flag */
275             SetCtrlVal (panel[3], DATA_RUNNO, replic+1); /* set rep cntr */
276             DefaultCtrl (panel[3], DATA_MSEV1);          /* clear out mse */
277             SetCtrlAttribute (panel[3], DATA_MSEV1, 6, 0);
278             DefaultCtrl (panel[3], DATA_MSEV2);
279             SetCtrlAttribute (panel[3], DATA_MSEV2, 6, 0);
280             DefaultCtrl (panel[3], DATA_MSEV3);
281             SetCtrlAttribute (panel[3], DATA_MSEV3, 6, 0);
282             DefaultCtrl (panel[3], DATA_MSEV4);
283             SetCtrlAttribute (panel[3], DATA_MSEV4, 6, 0);
284             DeletePlots (panel[3], DATA_REF1);           /* clear out plots */
285             Clear1D (max_knock, 5);
286             Clear1D (max_knock_pump, 5);        /* zero out summary arrays */
287             update();
288             temp_read (2);      /* temp loop 2 holds data for test var. */
289             cur_fit = DATA_MSEV1;   /* set mse to incre. for each fuel */
290             pump_val = DATA_GUESS1;/* set pump set to incre for each fuel */
291             GetCtrlVal (panel[3], DATA_NGAS_SW, &cnt); /* check if ngas on *
     /
292                if (cnt == 1)   {
293                   gas_valve(FALSE);                    /* delay 2 min if on */
```

Page 6     LG3M.C    Thu Apr '' 05:57:25 1995

```
294                    setpump (ref_pump_set);         /* set pump for refrnce */
295                    SetCtrlVal (panel[4], ABORT_TEST, "STABILIZING FROM GAS");
296                    wait (100.0);                    /* fuel and delay */
297                 }
298         /* fuel testing loop  - select fuel, test, increment              */
299            for ( fuel_num = 1; fuel_num <= samp; fuel_num++ ) {
300                if (ordr_rn == 1 && fuel_num == 3 && max_knock[4] == 0) {
301                   fuel_num ++;                  /*  run order green first */
302                   pump_val ++;          /* ordr_rn = run order 1 = green */
303                   cur_fit ++;
304                }
305                GetCtrlVal (panel[3], pump_val, &pump_set_est[fuel_num]);
306                valve (fuel_num);                            /* set valve */
307                SetCtrlVal (panel[3], DATA_OVER, over + ((timer() - st_time)/3
600.0));
308                maxknock (&max_knock[fuel_num], &pump_set_est[fuel_num],
309                       &max_knock_pump[fuel_num], fuel_num);/* maxknock rou
tine */
310                update ();              /* write test results to screen */
311                cur_fit++;                                     /* incr mse */
312                pump_val ++;                              /* incr pump set */
313                 if (fuel_num == 3 || fuel_num == 4) {   /* get PRF octanes *
/
314                    GetCtrlVal (panel[3], DATA_OCTANE1, &octane[1]);
315                    GetCtrlVal (panel[3], DATA_OCTANE2, &octane[2]);
316                   if ((ordr_rn == 0 || samp == 4) && fuel_num == 3 && abort_
flag == 0){
317                      octane[3] = (octane[2] - octane[1]) *  /* yellow fuel */
318                      ((max_knock[3] - max_knock[1]) /(max_knock[2] /* octane */
319                      - max_knock[1])) + octane[1];
320                      SetCtrlAttribute (panel[3], DATA_OCTANE3, 4, 0);
321                      SetCtrlVal (panel[3], DATA_OCTANE3, octane[3]);
322                   }
323                   if ((ordr_rn == 1 || samp == 4) && fuel_num == 4 && abort_f
lag == 0){
324                      octane[4] = (octane[2] - octane[1]) *   /* green fuel */
325                      ((max_knock[4] - max_knock[1]) /(max_knock[2]/* octane */
326                      - max_knock[1])) + octane[1];
327                      SetCtrlAttribute (panel[3], DATA_OCTANE4, 4, 0);
328                      SetCtrlVal (panel[3], DATA_OCTANE4, octane[4]);
329                   }
330                }
331             if ( ordr_rn == 1 && samp == 4 && fuel_num == 4) {
332                fuel_num = 2;/* if both samples, green first, then yellow *
/
333                pump_val --; pump_val --;
334                cur_fit --;
335             }
336             if (ordr_rn == 1 && samp == 4 && fuel_num == 3 && max_knock[3]
) 0.0)
337                fuel_num = 99;     /* green first, yellow then stop */
338
339             /* break out and return if ABORT pressed !! */
340             if (abort_flag == TRUE) {          /* abort if requested */
341                fuel_num = 99;                   /* cause for loop to end */
342                z = rep+1;                       /* "       "   reps  "  " */
343                valve (w_u);                     /* set valve to warm up fuel */
344                setpump(ref_pump_set);           /* set pump to init level */
345             }
346          }                                         /* end of fuel loop */
```

```
347
348            /* display/write data if good run */
349            if ( abort_flag == FALSE )   {
350              SetCtrlVal (panel[4], ABORT_TEST, "FORMATTING DATA");
351              if (samp == 4 || ordr_rn == 0)
352                log_faults (8," ");
353              if (samp == 4 || ordr_rn == 1)
354                log_faults (13," ");
355              diff2 = max_knock[1] - max_knock[2];   /* check for knk slope */
356              diff1 = octane[1] - octane[2];
357              slope = diff2/diff1;
358              if (slope > 0.0) {
359                error = ConfirmPopup ( "Are The Octanes for the PRF's Entered C
      orrectly ?");
360                if (error == 0)    {
361                  octane[0] = octane[1];
362                  octane[1] = octane[2];
363                  octane[2] = octane[0];
364                  SetCtrlVal (panel[3], DATA_OCTANE1, octane[1]);
365                  SetCtrlVal (panel[3], DATA_OCTANE2, octane[2]);
366                    octane[3] = (octane[2] - octane[1]) *
367                    ((max_knock[3] - max_knock[1]) /(max_knock[2]
368                    - max_knock[1])) + octane[1];
369                  SetCtrlVal (panel[3], DATA_OCTANE3, octane[3]);
370                    octane[4] = (octane[2] - octane[1]) *
371                    ((max_knock[4] - max_knock[1]) /(max_knock[2]
372                    - max_knock[1])) + octane[1];
373                  SetCtrlVal (panel[3], DATA_OCTANE4, octane[4]);
374                  if (samp == 4 || ordr_rn == 0)
375                  log_faults (8," Octanes were entered incorrectly");
376                  if (samp == 4 || ordr_rn == 1)
377                  log_faults (13," Octanes were entered incorrectly");
378                }
379              }
380
381                                              /* test for bracketing */
382              if ( ordr_rn == 0 || samp == 4)   {
383              if ((octane[2] > octane[1]) &&
384                ((octane[3] < octane[1] || octane[3] > octane[2]))) {
385                    MessagePopup ("Yellow Test Fuel Did Not Bracket");
386                    log_faults (8,"Test fuel did not bracket");
387              }
388              if ((octane[1] > octane[2]) && ((octane[3] < octane[2]
389              || octane[3] > octane[1])))    {
390                    MessagePopup ("Yellow Test Fuel Did Not Bracket");
391                    log_faults (8,"Test fuel did not bracket");
392              }
393              }
394
395              if (samp == 4 || ordr_rn == 1)  {
396              if ((octane[2] > octane[1]) &&
397                ((octane[4] < octane[1] || octane[4] > octane[2]))) {
398                    MessagePopup ("Green Test Fuel Did Not Bracket");
399                    log_faults (13,"Test fuel did not bracket");
400              }
401              if ((octane[1] > octane[2]) &&
402                ((octane[4] < octane[2] || octane[4] > octane[1]))) {
403                    MessagePopup ("Green Test Fuel Did Not Bracket");
404                    log_faults (13,"Test fuel did not bracket");
405              }
```

Page 8     LG3M.C   Thu Apr    05:57:25 1995

```
406                 }
407
408                 /* write knock data to replic arrays and display on summary */
409                     mxknk_1[replic] = max_knock[1];
410                     mxknk_2[replic] = max_knock[2];
411                     mxknk_3[replic] = max_knock[3];
412                     mxknk_4[replic] = max_knock[4];
413                     mxpmp_1[replic] = max_knock_pump[1];
414                     mxpmp_2[replic] = max_knock_pump[2];
415                     mxpmp_3[replic] = max_knock_pump[3];
416                     mxpmp_4[replic] = max_knock_pump[4];
417                     oct_3[replic] = octane[3];
418                     oct_4[replic] = octane[4];
419                     GetCtrlVal (panel[3], DATA_STD, &std);
420                     GetCtrlVal (panel[3], DATA_RATE, &rate);
421                     GetCtrlVal (panel[3], DATA_ENGNO, engno);
422                     GetCtrlVal (panel[5],CNFG_NET_DRV, drve);
423
424                 if ( ordr_rn == 0 || samp == 4)  {
425                     if (text_valy > FINAL_TEXT_9) /* reset data summ position*/
426                         text_valy = FINAL_TEXT_1;
427                     Fmt (num_dat, "%s(%i[w2]", replic+1);
428                     for (i=1; i<=3; i++) {
429                        Fmt (num_dat, "%s[a](%f[p1w9]%f[p1w8]%f[p0w8]",
430                           octane[i], max_knock[i], max_knock_pump[i]);
431                     }
432                   SetCtrlVal (panel[7], text_valy, num_dat);
433                   text_valy ++;              /* incr yell text data summary */
434                   Fmt (filen, "%s[w8](%s[t46t32t42t44t47t45]", desc1);
435                   Fmt (filen, "%s[a]<.%s", meth_nam);
436                   MakePathname ( drve, filen, path);   /* write data to file */
437                   file = OpenFile (path, 2, 1, 1);
438                   if ( file < 0) {          /* check for valid file handle */
439                      MessagePopup ("Could not open data file, check network");
440                      drve = "c:\\knock";
441                      MakePathname ( drve, filen, path);
442                      file = OpenFile ( path, 2, 1, 1);
443                   }
444                   error = FmtFile (file, "%f[p1]  %f[p1]  %f[p1] \n %i \n", octa
      ne[1],
445                      octane[2], octane[3], replic+1);
446                   error = FmtFile (file, "%s %s %f[p1] %s ", datestr(), timestr(
      ),
447                      baro, oper);
448                   error = FmtFile (file, "%s %s %f[p0] %f[p1] ", meth_nam, engno
      , over, std);
449                   error = FmtFile (file, "%f[p1] %f[p0] %f[p0] \n", rate, itemp,
      mtemp);
450                   error = CloseFile (file);
451                 }
452
453                 if (samp == 4 || ordr_rn == 1)  {
454                     if (text_valg > FINAL_TEXT_9) /* reset data summ position*/
455                         text_valg = FINAL_TEXT_1;
456                     Fmt (num_dat, "%s(%i[w2]", replic+1);
457                     for (i=1; i<=2; i++) {
458                        Fmt (num_dat, "%s[a](%f[p1w9]%f[p1w8]%f[p0w8]",
459                           octane[i], max_knock[i], max_knock_pump[i]);
460                     }
461                        Fmt (num_dat, "%s[a](%f[p1w9]%f[p1w8]%f[p0w8]",
```

Page 9    LG3M.C  Thu Apr `` 05:57:25 1995

```
462                     octane[4], max_knock[4], max_knock_pump[4]);
463                 SetCtrlVal (panel[12], text_valg, num_dat);
464                 text_valg ++;               /* incr green text data summary */
465                 Fmt (filen, "%s[w8](%s[t46t32t42t44t47t45]", desc2);
466                 Fmt (filen, "%s[a](.%s", meth_nam);
467                 MakePathname ( drve, filen, path);   /* write data to file */
468                 file = OpenFile (path, 2, 1, 1);
469                     if ( file < 0) {        /* check for valid file handle */
470                 MessagePopup ("Could not open data file, check network");
471                 drve = "c:\\knock";
472                 MakePathname ( drve, filen, path);
473                 file = OpenFile ( path, 2, 1, 1);
474                 }
475                 error = FmtFile (file, "%f[p1]  %f[p1]  %f[p1] \n %i \n", octa
    ne[1],
476                 octane[2], octane[4], replic+1);
477                 error = FmtFile (file, "%s %s %f[p1] %s ", datestr(), timestr(
    ),
478                 baro, oper);
479                 error = FmtFile (file, "%s %s %f[p0] %f[p1] ", meth_nam, engno
    , over, std);
480                 error = FmtFile (file, "%f[p1] %f[p0] %f[p0] \n", rate, itemp,
     mtemp);
481                 error = CloseFile (file);
482             }
483             adj_offset = max_knock_pump[1] - offset_pump;
484             SetCtrlVal (panel[3], DATA_GUESS1, adj_offset);
485             adj_offset = max_knock_pump[2] - offset_pump;
486             SetCtrlVal (panel[3], DATA_GUESS2, adj_offset);
487             adj_offset = max_knock_pump[3] - fuel_offset;
488             SetCtrlVal (panel[3], DATA_GUESS3, adj_offset);
489             adj_offset = max_knock_pump[4] - fuel_offset;
490             SetCtrlVal (panel[3], DATA_GUESS4, adj_offset);
491             replic ++;                      /* increment loop counter */
492         }                                   /* end of abort_false loop */
493
494         SetCtrlAttribute (panel[7], text_valy, 4, 15); /* reset for next
    */
495         SetCtrlAttribute (panel[12], text_valg, 4, 15); /* knock shft */
496     }                                       /* end of replic loop */
497
498     if (abort_flag == FALSE)  { /* abort false loop, all reps cmplt */
499         valve (w_u);                    /* set valve to warm up fuel */
500         setpump(ref_pump_set);              /* set pump to init level */
501         if (diff2 < 0.0)            /* test for knock sensitivity */
502         diff2 = -diff2;
503         if (octane[1] 80.0 && diff2 < 4.0)
504         MessagePopup ( "The Difference in Knock Level For the PRF's is L
    ow");
505
506         if (prt == 1) {         /* if auto print, print data screens */
507             orde = ordr_rn;                 /* set print order    */
508             for (i=3; i<=samp; i++) {       /* loop for # of panels */
509                 if (orde == 1)
510                 pnl = panel[12];
511                 else
512                 pnl = panel[7];
513                 final_data (pnl, 1, std, rate, meth_nam, replic,
514                 engno, over);           /* call final, mode print only */
515                 if (samp == 4 && orde == 1)
```

```
Page 10    LG3M.C Thu Apr    05:57:25 1995

516                    orde --;
517                    if (samp == 4 && orde == 0)
518                      orde ++;
519                    HidePanel (pnl);
520                  }
521                  DisplayPanel (panel[3]);
522                }                                /* end of auto print loop */
523              end_time = Timer();
524              Fmt (tmp,"Test Complete %s", TimeStr());
525              SetCtrlAttribute (panel[4], ABORT_INDIC,7,0);
526              SetCtrlVal (panel[4], ABORT_TEST, tmp);
527              SetCtrlAttribute (panel[4], ABORT_ABORT,0,"OK");
528              err = 0;
529              cnt = 0;
530            while (err == 0) {        /* routine for gas valve end of test */
531              err = GetUserEvent (0, &handle, &id);
532              SetCtrlVal (panel[3], DATA_OVER, over + ((timer() - st_time)/360
         0.0));
533              SetCtrlVal (panel[3], DATA_TIME, timestr());
534              if (Timer() - end_time ) 90.0 && cnt == 0) {
535                gas_valve (TRUE);
536                GetCtrlVal (panel[3], DATA_NGAS_SW, &cnt);
537                SetCtrlVal (panel[4], ABORT_TEST, tmp);
538              }
539            }
540            /* TOLUENE FUEL CALIBRATION AND CHECK */
541              Fmt (tol, "%s(%f[p1]", std);
542              MakePathname ("c:\\keas\\tol", tol, path);
543              file = OpenFile (path, 1, 2, 1);
544              ScanFile (file, "%s>%4f[x]",tol_std);
545              error = SetFilePtr ( file, 0, 0);
546              error = CloseFile (file);
547
548            if (samp == 4 || ordr_rn == 0)    /* yellow test fuel for TSF */
549              if ((octane[3] )= tol_std[1]) || (octane[3] (= tol_std[0])) {
550                diff1 = 100.0;
551                Fmt ( filen, "%s(TSF.%s", meth_nam);/* slct TSF for smple*/
552                MakePathname ("c:\\keas\\tol", filen, path);
553                file = OpenFile (path, 1, 2, 1);
554                for (i=0; i<=10; i++)  {
555                  ReadLine (file, tmp, 6);
556                  Scan (tmp, "%s>%f[p1]", &tsf);
557                  diff2 = octane[3] - tsf;
558                  diff2 = fabs (diff2);
559                  if ( diff2 ( diff1) {
560                    diff1 = diff2;
561                    tsf1 = tsf;
562                  }
563                }
564                SetFilePtr (file, 0, 0);
565                CloseFile (file);
566                Fmt(tmp, "The %f[p1] TSF is not correct for the %s sample\n",
         std, desc1);
567                Fmt ( tmp, "%s[a](A %f TSF should be used for calibration. ",
         tsf1);
568                SetCtrlVal (panel[6], ERROR_TEXT, tmp);
569                InstallPopup (panel[6]);
570                GetPopupEvent(TRUE,&id);
571                DefaultCtrl (panel[6], ERROR_TEXT);
572                RemovePopup (0);
```

Page 11  LG3M.C  Thu Apr 1? 05:57:25 1995

```
573                   log_faults (8," Incorrect TSF was used ");
574              }
575
576              if (samp == 4 || ordr_rn == 1)      /* Green test fuel for TSF */
577                if ((octane[4] >= tol_std[1]) || (octane[4] <= tol_std[0])) {
578                  diff1 = 100.0;
579                  Fmt ( filen, "%s(TSF.%s", meth_nam);/* slct TSF for smple*/
580                  MakePathname ("c:\\keas\\tol", filen, path);
581                  file = OpenFile (path, 1, 2, 1);
582                  for (i=0; i<=10; i++) {
583                    ReadLine (file, tmp, 6);
584                    Scan (tmp, "%s>%f[p1]", &tsf);
585                    diff2 = octane[4] - tsf;
586                    diff2 = fabs (diff2);
587                    if ( diff2< diff1) {
588                      diff1 = diff2;
589                      tsf1 = tsf;
590                    }
591                  }
592                  SetFilePtr (file, 0, 0);
593                  CloseFile (file);
594                  Fmt (tmp, "The %f[p1] TSF is not correct for the %s sample\n", std, desc2);
595                  Fmt ( tmp, "%s[a](A %f TSF should be used for calibration. ", tsf1);
596                  SetCtrlVal (panel[6], ERROR_TEXT, tmp);
597                  InstallPopup (panel[6]);
598                  GetPopupEvent(TRUE,&id);
599                  DefaultCtrl (panel[6], ERROR_TEXT);
600                  RemovePopup (0);
601                  log_faults (13," Incorrect TSF was used ");
602                }
603
604              if ((rate > tol_std[3]) || (rate < tol_std[2])) {
605                Fmt (tmp, " The rating of %f[p1] is outside of the allowed\n", rate);
606                Fmt ( tmp, "%s[a]< tuning limits for the %f[p1]", std);
607                Fmt ( tmp, "%s[a]< TSF.\n The current tuning limits for the");
608                Fmt ( tmp, "%s[a]< %f[p1] TSF\n are from %f[p1] to", std, tol_std[2]);
609                Fmt ( tmp, "%s[a]< %f[p1].", tol_std[3]);
610                SetCtrlVal (panel[6], ERROR_TEXT, tmp);
611                InstallPopup (panel[6]);
612                GetPopupEvent(TRUE,&id);
613                DefaultCtrl (panel[6], ERROR_TEXT);
614                RemovePopup (0);
615                if (samp == 4 || ordr_rn == 0)
616                  log_faults (8," TSF rating beyond limits ");
617                if (samp == 4 || ordr_rn == 1)
618                  log_faults (13," TSF rating beyond limits ");
619              }
620
621          }                 /* end of abort = false loop - replic completed*/
622          HidePanel (panel[4]);                    /* hide abort panel */
623          DefaultPanel (panel[4]);
624          SetCtrlAttribute (panel[4], ABORT_ABORT, 0, "ABORT");
625          SetCtrlAttribute (panel[3], DATA_DESC1, 10, 2);/*reset hot on*/
626          SetCtrlAttribute (panel[3], DATA_DESC2, 10, 2);/* desc lines */
627          SetCtrlAttribute (panel[3], DATA_RUN, 16, 0);/*display hidden*/
```

Page 12    LG3M.C  Thu Apr 17 05:57:25 1995

```
628           SetCtrlAttribute (panel[3], DATA_GRN, 16, 0);        /* buttons */
629           SetCtrlAttribute (panel[3], DATA_RETURN, 16, 0);
630           SetCtrlAttribute (panel[3], DATA_TEMPR, 16, 0);
631           SetCtrlAttribute (panel[3], DATA_HELPR_1, 16, 0);
632           SetCtrlAttribute (panel[3], DATA_YLW, 16, 0);
633           SetCtrlAttribute (panel[3], DATA_CONFG, 16, 0);
634           SetActivePanel (panel[3]);            /* set cursor to SSON menu */
635           CopyString (desc_old, 0, desc1, 0, 8); /* copy name for incr */
636           CopyString (desc_old2, 0, desc2, 0, 8);/* copy name for incr */
637           SetActiveCtrl (DATA_RUN);             /* replicate number */
638           break;
639         case DATA_RETURN:                       /* back to main menu */
640           HidePanel (panel[3]);                 /* hide DATA panel */
641           HidePanel (panel[1]);
642           return;
643           break;
644         default:
645           break;
646         case DATA_GRN:
647           final_data (panel[12], 0, std, rate, meth_nam, replic,
648               engno, over);
649           break;
650         case DATA_TEMPR:
651           DisplayPanel (panel[1]);
652           SetActivePanel (panel[1]);
653           error = 0;
654           while (error == 0)     {
655             temp_read (0);
656             Delay (0.5);
657             error=GetUserEvent (0, &handle, &id);
658           }
659           SetCtrlAttribute (panel[1], TEMP_OILTEMP, 6, 7);
660           SetCtrlAttribute (panel[1], TEMP_WTEMP, 6, 7);
661           HidePanel (panel[1]);
662           DisplayPanel (panel[3]);
663           break;
664         case DATA_HELPR_1:
665           InstallPopup (panel[8]);
666           help_read (panel[8]);
667           RemovePopup (0);
668           break;
669         case DATA_YLW:
670           final_data (panel[7], 0, std, rate, meth_nam, replic,
671               engno, over);
672           break;
673         case DATA_CONFG:
674           HidePanel (panel[3]);
675           confg ();
676           k=0;                    /* reset data flag to update run parm */
677           break;
678         case DATA_OCTANE1:                      /* head setting routines */
679         case DATA_OCTANE2:
680           head_set ();
681           break;
682         case DATA_NGAS_SW:                      /* natural gas control routine */
683           GetCtrlVal (panel[3], DATA_NGAS_SW, &cnt);
684           gas_valve (cnt);
685           break;
686         case DATA_DR1:                          /* fuel drain control routines */
687           GetCtrlVal (panel[3], DATA_DR1, &cnt);
```

Page 13    LG3M.C  Thu Apr 1~ 05:57:25 1995

```c
688                drain_valve ("e", cnt);
689                break;
690            case DATA_DR2:
691                GetCtrlVal (panel[3], DATA_DR2, &cnt);
692                drain_valve ("f", cnt);
693                break;
694            case DATA_DR3:
695                GetCtrlVal (panel[3], DATA_DR3, &cnt);
696                drain_valve ("g", cnt);
697                break;
698            case DATA_DR4:
699                GetCtrlVal (panel[3], DATA_DR4, &cnt);
700                drain_valve ("h", cnt);
701                break;
702          }
703       }
704    }                                                      /* end of runsson */
705    void confg ( void )
706    {
707       char nm_1[13];
708       int i, dat_val, dat1_val;
709       DisplayPanel(panel[2]);                              /* show config panel */
710
711       while (TRUE)   {
712        GetUserEvent(TRUE,&handle,&id);                     /* check for user input */
713         switch (id) {
714           case CONFIG_ACCEPT:                              /* done with config panel */
715             dat_val = CONFIG_SAMPL1;
716             dat1_val = DATA_DESC1;
717
718             for ( i=1; i<=2; i++) {
719               GetCtrlVal (panel[2], dat_val, nm_1);        /* get file name */
720               SetCtrlVal (panel[3], dat1_val, nm_1);       /* copy file info to */
721               dat_val ++; dat1_val ++; dat1_val ++;        /* run screen */
722             }
723             SetCtrlAttribute(panel[3], DATA_YLW, 15, 1);   /* enable data */
724             SetCtrlAttribute(panel[3], DATA_GRN, 15, 1);        /* buttons */
725             SetCtrlAttribute(panel[3], DATA_DESC1, 15, 1);
726             SetCtrlAttribute(panel[3], DATA_DESC3, 15, 1);
727             SetCtrlAttribute(panel[3], DATA_DESC2, 15, 1);
728             SetCtrlAttribute(panel[3], DATA_DESC4, 15, 1);
729             SetCtrlAttribute (panel[3], DATA_GUESS3, 15, 1);
730             SetCtrlAttribute (panel[3], DATA_GUESS4, 15, 1);
731             HidePanel(panel[2]);                           /* hide config panel */
732             return;
733             break;
734           case CONFIG_MORE:
735             HidePanel(panel[2]);
736             DisplayPanel(panel[5]);
737             while (TRUE)    {
738               GetUserEvent(TRUE,&handle,&id);              /* check for user input */
739               switch (id) {
740               case CNFG_RETURN:                            /* done with config panel */
741                 GetCtrlVal (panel[5], CNFG_W_U, &w_u);
742                 valve ( w_u );                             /* set valve to warm up fuel */
743                 GetCtrlVal (panel[5], CNFG_REFPUMP, &ref_pump_set);
744                 SavePanelState(panel[5], "c:\\keas\\pnl\\cnfgm.pnl");
745                 HidePanel(panel[5]);                       /* hide config panel */
746                 return;
747                 break;
```

Page 14    LG3M.C  Thu Apr '' 05:57:25 1995

```
748                case CNFG_HELP_R:
749                  InstallPopup (panel[9]);
750                  help_read (panel[9]);
751                  RemovePopup (0);
752                  break;
753              }
754            }
755            break;
756          case CONFIG_HELP_1:
757            InstallPopup (panel[10]);
758            help_read (panel[10]);
759            RemovePopup (0);
760            break;
761        }
762      }
763    }                                                    /* end of config */
764
765    void maxknock (double *max_knock,int *initial_guess,double *max_knk_pmp_set,
766      int fuel_num)
767    {
768      int prev_pump_set;
769      int dir_change, samples, color[5];
770      double maxknock_array[15];              /* data collection "Y" values */
771      double pumpset_array[15];               /* data collection "X" values */
772      float curve_fit_Y[21];                   /* "Y" values for curve fit */
773      float curve_fit_X[21];                   /* "X" values for curve fit */
774      double bfda[15];                              /* best fit  data array */
775      double bfca[5];                        /* best fit coefficient array */
776      double cur_knock_level, cur_pump_set, sys_time;
777      double prev_knock_level, cur_samp_intvl, cur_fuel_intvl, range;
778      double mse;                            /* mean sq'd error for PolyFit */
779      double x1;                    /* vars for local max/min detrmination */
780      double x2;                    /* vars for local max/min detrmination */
781      double y1;                    /* vars for local max/min detrmination */
782      double y2;                    /* vars for local max/min detrmination */
783      double max_x;                     /* max value of array from MaxMin */
784      int d, d1;               /* location ( array index ) for max or min */
785      double min_n;                     /* min value of array from MaxMin */
786      int i, lpt;                                          /* loop index */
787      int done;                         /* data collection complete flag */
788      double sens;                   /* var for sensitivity adjustment */
789      int warm_up_delay;                       /* fuel switching delay */
790      int mxk_delay;                          /* max knock delay peroid */
791      cur_pump_set = *initial_guess;          /* start at initial guess */
792      prev_pump_set = cur_pump_set;
793      dir_change = 0;                       /* no direction changes yet */
794      sample_index = 0;                 /* no knock readings taken yet */
795      cur_knock_level = 0;                         /* no knock data yet */
796      lpt = 0;                            /* set plot delete indicator */
797      cnt_1 = 0;                                 /* minimum KI counter */
798      color[1] = 12; color[2] = 9; color[3] = 14; color[4] = 10;
799      stat_flag = 0;        /* flag = 6 minimum data points; 5 rich-lean */
800            /* 1 minimum knock intensity; -1 DAQ stopped; 0 everything ok */
801
802      GetCtrlVal(panel[5],CNFG_PINTVL, &cur_samp_intvl); /* PRF pmp intrvl */
803      GetCtrlVal(panel[5],CNFG_FINTVL, &cur_fuel_intvl); /* smpl pmp intvl */
804      GetCtrlVal(panel[5],CNFG_NSAMPLE, &samples);/* sets number of curves */
805      GetCtrlVal(panel[5],CNFG_WMDELAY, &warm_up_delay); /* fuel swtchg dly*/
806      GetCtrlVal (panel[5],CNFG_SENS, &sens);    /* knock sens. adjustment */
```

```
Page 15    LG3M.C  Thu Apr 1? 05:57:25 1995

807      GetCtrlVal (panel[5], CNFG_DLY, &mxk_delay);    /* get maxknock delay */
808      if (fuel_num == 3 || fuel_num == 4)   /* change pump intvl for sample */
809        cur_samp_intvl = cur_fuel_intvl;
810      done = FALSE;
811
812      setpump (cur_pump_set);                          /* start at initial guess */
813      sys_time = timer ();                             /* run on warmup fuel */
814      SetCtrlVal (panel[4], ABORT_TEST, "ENGINE STABILIZING");
815      while (timer () < sys_time + warm_up_delay)   {
816        GetUserEvent (0, &handle, &id);                /* check for user input */
817        abort_check ( &handle, &id );
818        if (abort_flag == TRUE)                        /* abort if requested */
819          return;
820        temp_read(1);                                  /* get temperatures */
821      }
822
823      while ( !done )  {
824        if (sample_index > 14)     {    /* flag for overflow of data arrays */
825          MessagePopup ("Data arrays are full adjust pump setting");
826          abort_flag = TRUE;
827          return;
828        }
829        setpump (cur_pump_set);                        /* set pump where you want it */
830        if (stat_flag > 0) {                           /* stabilize if necessary */
831          SetCtrlVal (panel[4], ABORT_TEST, "ENGINE STABILIZING");
832          delay(stat_flag);                            /* delay for minimum data */
833        }
834        stat_flag = 0;                                 /* reset control flag */
835        SetCtrlVal (panel[4], ABORT_TEST, "ACQUIRING KNOCK");
836        sample (&cur_knock_level, samples);            /* get knock samples */
837        GetUserEvent (0, &handle, &id);                /* check for user input */
838        abort_check ( &handle, &id );
839        if (abort_flag == TRUE)     /* abort if requested in sample fnctn */
840          return;
841        maxknock_array[sample_index] = cur_knock_level;/* update knock array */
842        pumpset_array[sample_index] = cur_pump_set;    /* update pump array */
843
844                    /* display data */
845        if (stat_flag != 1 || stat_flag != -1)   {    /* plot good data */
846          DeleteGraphPlot (panel[3], DATA_REF1, lpt, 1);
847          lpt = PlotXY (panel[3], DATA_REF1, pumpset_array, maxknock_array,
848                  (sample_index + 1), 4, 4, 2, 1, 1, color[fuel_num]);
849        }
850        if (cnt_1 > 10)    {    /* after 10 auto pump setting abort test */
851          MessagePopup ("KI low. Check Fuel Level. ABORTING");
852          abort_flag = TRUE;
853          return;
854        }
855
856        if (stat_flag == 0)  {                         /* if stat ok process data */
857
858                    /* RICH - LEAN OPERATION
859          reverse direction if negative slope on first three samples,
860          revert to initial guess values and continue.    */
861          if ( (sample_index == 2) && ((maxknock_array[0] > maxknock_array[1])
862              && (maxknock_array[1] > maxknock_array[2]) ) )
863          {
864            cur_samp_intvl = -cur_samp_intvl;          /* make interval negative */
865            cur_pump_set = *initial_guess;             /* restore first pump set */
```

Page 16   LG3M.C  Thu Apr 1  05:57:25 1995

```
866             cur_knock_level = maxknock_array[0];/* restore first knock level */
867             stat_flag = 5;                  /* set direction change flag and delay */
868         }
869
870                     /* MINIMUM DATA LOOP
871     check for direction change after 2 samples.  decrease initial setting
872     and start over. if (5 data points revert to (initial -1.7) pump & knock
873     levels then continue */
874         if ( (sample_index == 2) && ((maxknock_array[0] < maxknock_array[1])
875             && (maxknock_array[1] - maxknock_array[2] > sens) ) ) {
876             cur_pump_set = (*initial_guess - (1.7*cur_samp_intvl));
877             stat_flag = 6;                  /* set minimum data flag */
878             DeleteGraphPlot (panel[3], DATA_REF1, 1pt, 1);
879         }
880
881                     /* DIRECTION CHANGE
882             Increment Direction Change Flag */
883         if ( (sample_index > 2) && (cur_knock_level < prev_knock_level) )
884             dir_change++;
885
886                     /* DONE SEQUENCE
887     we're done if more than 4 loops and there was a direction change*/
888         if ( (dir_change >= 1) && ((prev_knock_level - cur_knock_level)
889             > sens) || dir_change >= 2 )
890             done = 1;
891     }                                       /* end of stat == 0 loop */
892     if (stat_flag != 6 || stat_flag != -1)       /* if not min. data */
893         cur_pump_set += cur_samp_intvl;         /* or daq stop incr pump */
894                                                 /* increment sample interval */
895
896     if (stat_flag == 0 || stat_flag == 5) {      /* if rich or ok */
897         prev_knock_level = cur_knock_level;     /* save last settings */
898         prev_pump_set = cur_pump_set;           /* save last settings */
899         sample_index ++;                        /* bump sample index */
900     }
901     else if (stat_flag == 1 || stat_flag == 6)
902         sample_index = 0;                       /* reset sample index */
903     }                                           /* end of while loop */
904
905                     /* CURVE FIT ROUTINE */
906     PolyFit (pumpset_array, maxknock_array, sample_index, 3, bfda, bfca, &mse);
907     /* take derivative, set == zero and solve for X, the max pump setting*/
908     x1 = (-2.0 * bfca[2] + pow (4.0 * pow (bfca[2], 2.0) - 12.0 * bfca[3]
909         * bfca[1], 0.5)) / (6.0 * bfca[3]);
910     x2 = (-2.0 * bfca[2] - pow (4.0 * pow (bfca[2], 2.0) - 12.0 * bfca[3]
911         * bfca[1], 0.5)) / (6.0 * bfca[3]);
912     /* calculate Y, the max knock, from X, the max knock pump setting */
913     y1 = bfca[0] + bfca[1] * x1 + bfca[2] * pow (x1, 2.0) + bfca[3]
914         * pow (x1, 3.0);
915     y2 = bfca[0] + bfca[1] * x2 + bfca[2] * pow (x2, 2.0) + bfca[3]
916         * pow (x2, 3.0);
917
918     if (y1 > y2)  {         /* check which Y ( + or - ) is greater and pick */
919         cur_pump_set = x1;                      /* X accordingly */
920         *max_knk_pmp_set = x1;
921     }
922     else  {
923         cur_pump_set = x2;
```

```
Page 17    LG3M.C  Thu Apr 1  05:57:25 1995

924         *max_knk_pmp_set = x2;
925      }
926      setpump (cur_pump_set);  /* set pump at calc'd max knock pump setting */
927      SetCtrlVal (panel[4], ABORT_TEST, "ACQUIRING MAXKNOCK");
928      delay(mxk_delay);                              /* delay for max knock */
929      if ( fuel == 1 || test_type == 0) /* get knock value based on test type
     */
930         sample (max_knock, 2);      /* 128 samples for mon or leaded fuels */
931      else
932         sample (max_knock, 1);
933      GetUserEvent (0, &handle, &id);              /* check for user input */
934      abort_check ( &handle, &id );
935      if (abort_flag == TRUE)   /* abort if requested in sample function */
936         return;
937
938                         /* compare calc max knock with actual max knock */
939      cur_knock_level = *max_knock;
940      if ( y1 > y2)
941         y2 = y1;
942      range = y2 * 0.025;              /* 5% var for calc max vs. max knk */
943      if (fuel == 1)                               /* allow for leaded fuels */
944         range = y2 * 0.1;
945      if (cur_knock_level > (y2 + range ) ||
946         cur_knock_level < (y2 - range))  {
947         SetCtrlAttribute (panel[3], cur_fit, 6, 4);
948         if (fuel_num == 1 || fuel_num == 2 || fuel_num == 3)
949            SetCtrlAttribute (panel[7], text_valy, 4, 4);
950         if (fuel_num == 1 || fuel_num == 2 || fuel_num == 4)
951            SetCtrlAttribute (panel[12], text_valg, 4, 4);
952      }
953                      /* find max/min values of pump setting actually ran */
954      MaxMin (pumpset_array, sample_index, &max_x, &d, &min_n, &d1);
955         /* generate array to depict curve fit within bounds of max/min */
956      for (i = 0; i <= 20; i++)  {
957         curve_fit_X[i] = min_n + (float)i * (max_x - min_n) / 20.0;
958         curve_fit_Y[i] = bfca[0] + bfca[1] * curve_fit_X[i]
959                       + bfca[2] * pow (curve_fit_X[i], 2.0)
960                       + bfca[3] * pow (curve_fit_X[i], 3.0);
961      }
962                                              /* plot curve fit results */
963      PlotXY (panel[3], DATA_REF1, curve_fit_X, curve_fit_Y,
964             i, 3, 3, 0, 0, 1, color[fuel_num]);
965      SetCtrlVal (panel[3], cur_fit, mse);
966      GetUserEvent (0, &handle, &id);              /* check for user input */
967      abort_check ( &handle, &id );
968      if (abort_flag == TRUE)   /* abort if requested in sample function */
969         return;
970   }                                               /* end of max knock */
971
972   void abort_check ( int *handle, int *id )
973   {
974      int stat;
975
976      if ( *handle == panel[4])      {      /* if input is from abort panel */
977         switch (*id) {
978            case ABORT_ABORT:
979               abort_flag = TRUE;                        /* set ABORT flag! */
980               return;
981               break;
982            default:
```

Page 18    LG3M.C    Thu Apr    05:57:25 1995

```
 983          break;
 984        }
 985      }
 986      else if (*handle == panel[3])   {                  /* drain valve sequence */
 987        GetCtrlVal (panel[3], *id, &stat);
 988        switch (*id)   {
 989          case DATA_DR1:
 990            drain_valve ("e", stat);
 991            break;
 992          case DATA_DR2:
 993            drain_valve ("f", stat);
 994            break;
 995          case DATA_DR3:
 996            drain_valve ("g", stat);
 997            break;
 998          case DATA_DR4:
 999            drain_valve ("h", stat);
1000            break;
1001        }                                                /* end switch loop */
1002      }                                                  /* end panel[3] if loop */
1003    }                                                    /* end of abort_check */
1004
1005    void valve (int vs)
1006    {
1007      char serial_dat[4];
1008      int pos, color, cnt;
1009      pos = 0;
1010      cnt = 0;
1011
1012      while (pos != vs && cnt <=3)   {
1013        SetCtrlVal (panel[4], ABORT_TEST, "VALVE SWITCHING");
1014        Fmt (serial_dat, "%s(%i9\r", vs);
1015        rs_comm (PORTA, serial_dat);
1016         Scan(up_ld,"%s)%i[w1]",&pos);
1017        if (pos == 1)
1018          color = 12;
1019        else if (pos == 2)
1020          color = 9;
1021        else if (pos == 3)
1022          color = 14;
1023        else if (pos == 4)
1024          color = 10;
1025        SetCtrlAttribute (panel[4], ABORT_INDIC, 7, color);
1026        cnt ++;
1027      }
1028      if (cnt >= 3)
1029        err_routine ("Valve Pos", 99);
1030      return;
1031    }                                                    /* end of valve */
1032
1033    void setpump (double desired_pump_set)
1034    {
1035      int delay_time;
1036      char pmp_stg[10];
1037
1038      SetCtrlVal (panel[4], ABORT_TEST, "SETTING PUMP");
1039
1040      if (desired_pump_set > 1400.0) {/* 14000 is the max allowed pmp stng */
1041        desired_pump_set = 1400.0;                        /* no exceptions!! */
1042        MessagePopup ("Pump at maximum. To continue install larger pump");
```

Page 19    L63M.C  Thu Apr 1? 05:57:25 1995

```
1043         abort_flag = TRUE;
1044         return;
1045       }
1046     if (up_pump > desired_pump_set*10+10) {          /* decrease pump */
1047       SetCtrlAttribute (panel[4], ABORT_TEST, 4, 12);
1048       Fmt (pmp_stg,"%s<KR%f[p0]\n", (desired_pump_set*10.0)-200.0);
1049       rs_comm(PORTB,pmp_stg);
1050       wait((desired_pump_set - up_pump/10) / 50.0+2.0);
1051     }
1052     SetCtrlAttribute (panel[4], ABORT_TEST, 4, 10);    /* increase pump */
1053       while (up_pump > desired_pump_set*10+10 ||
1054              up_pump < desired_pump_set*10-10) {
1055         Fmt (pmp_stg,"%s<KR%f[p0]\n", (desired_pump_set*10));
1056         rs_comm(PORTB,pmp_stg);
1057         Scan(up_1d,"%s)%f[p0]",&up_pump);
1058         wait((desired_pump_set - up_pump/10) / 150.0+1);
1059       }
1060
1061     if (fuel == 1)                      /* increase delay for leaded fuels */
1062        delay (3.0);
1063     SetCtrlAttribute (panel[4], ABORT_TEST, 4, 15);
1064     return;
1065   }                                             /* end of setpump */
1066
1067 void sample (double *ckl, int events_sampled)
1068 {
1069   int i, j, mess_off;
1070   int count, count_2, min_ind, max_ind, tm_base, samp_intv, wparm;
1071   int daq_stat, hand_1;
1072   long lparm, daq_index;
1073   double max_knk_sig, min_knk_sig, sum_knk, rng, thres_lvl;
1074
1075   count = 0;
1076   count_2 = 0;
1077   rng = 0.0;
1078   sum_knk = 0.0;
1079   GetCtrlVal (panel[5], CNFG_THRES, &thres_lvl);
1080   error = Config_Alarm_Deadband (1, 0, "AI0", 0.25, 0.2, 1, 1, 9, 0);
1081     if (error != 0)
1082       err_routine ("Alarm Deadband", error);
1083   error = DAQ_StopTrigger_Config (1, 1, 5);
1084     if (error != 0)
1085       err_routine ("Stop Trigger", error);
1086   error = DAQ_Rate (25000.0, 0, &tm_base, &samp_intv);
1087     if (error != 0)
1088       err_routine ("DAQ RATE", error);
1089   error = DAQ_Start (1, 0, 1, circ_dat, 500L, tm_base, samp_intv);
1090     if (error != 0)
1091       err_routine ("DAQ START", error);
1092
1093   j = round (pow (2.0, events_sampled) * 32.0 - 1.0);
1094   Clear1D (maxnok_dat, 129);                  /* clear data array */
1095   for (i = 0; i <= j; i++) {
1096     mess_off = 1;
1097     max_knk_sig = 0.0;
1098     error = Config_DAQ_Event_Message (0, 0, "0", 0, 0, 0, 0, 0, 0, 0, 0, 0);
1099     error = Get_DAQ_Event (0, &hand_1, &mess_off, &wparm, &lparm);
1100     DAQ_Monitor (1, 0, 0, 250L, sect_dat, &daq_index, &daq_stat);
1101       if (daq_stat != 0) {      /* if DAQ stopped return and reset */
```

Page 20   LG3M.C   Thu Apr 1~ 05:57:25 1995

```
1102              stat_flag = -1;
1103              return;
1104            }
1105            switch (mess_off) {
1106            case 9:                    /* if soft trgr detects knock, process knock */
1107              DAQ_VScale (1, 0, 1, 0.02, 0.0, 250, sect_dat, y_doubl);
1108              Bw_LPF (y_doubl, 250, 25000.0, 1800.0, 4, y_doubl);
1109              MaxMin1D (y_doubl, 250, &max_knk_sig, &max_ind, &min_knk_sig, &min_ind);
1110              maxnok_dat[i] = max_knk_sig;
1111              if ( max_knk_sig > thres_lvl )   {
1112                Sum1D (maxnok_dat, i+1, &sum_knk);
1113                sum_knk = sum_knk/(i+1);            /* moving average on maxnok */
1114                rng = sum_knk * 0.2;
1115                if ( max_knk_sig > (sum_knk + rng) ||
1116                   (max_knk_sig < (sum_knk - rng)) )
1117                  i --;
1118                else
1119                  PlotStripChart (panel[3], DATA_KI, maxnok_dat, 1, i, 0, 4);
1120              }
1121              else if ( max_knk_sig < thres_lvl ) {
1122                i --;                   /* if below threshold decrement loop counter */
1123                if (sample_index == 0)             /* if init smpl loop incr */
1124                  count_2 ++;                       /* low KI incr counter */
1125              }
1126              count = 0;                            /* reset no knock counter */
1127              break;
1128            case 1:                                 /* if no knock trigger */
1129            default:
1130              i--;                                  /* adjust counter */
1131              count ++;
1132              break;
1133            }                                       /* end of switch */
1134            if ( count > 700 || count_2 > 10 ) {    /* if false trigger > 700 */
1135              cnt_1 ++;                             /* or low KI > 10 stop DAQ incr pump */
1136              DAQ_Clear (1);
1137              stat_flag = 1;
1138              return;
1139            }
1140          }                                         /* end of data collection loop */
1141          Mean (maxnok_dat, j+1, ck1);
1142          DAQ_Clear (1);
1143          return;                                   /* return average as the finished result */
1144        }                                           /* end of sample */
1145        void update ( )
1146        {
1147          char *scratch;
1148          scratch = "            ";
1149
1150                                                    /* write results to DATA panel */
1151          Fmt ( scratch, "%s(%f[p1]", max_knock[1]);
1152          SetCtrlVal (panel[3], DATA_MAXKNOCK1, scratch);
1153          Fmt ( scratch, "%s(%f[p1]", max_knock[2]);
1154          SetCtrlVal (panel[3], DATA_MAXKNOCK2, scratch);
1155          Fmt ( scratch, "%s(%f[p1]", max_knock[3]);
1156          SetCtrlVal (panel[3], DATA_MAXKNOCK3, scratch);
1157          Fmt ( scratch, "%s(%f[p1]", max_knock[4]);
1158          SetCtrlVal (panel[3], DATA_MAXKNOCK4, scratch);
1159          Fmt ( scratch, "%s(%f[p0]", max_knock_pump[1]);
1160          SetCtrlVal (panel[3], DATA_MAXPUMP1, scratch);
```

Page 21   LG3M.C   Thu Apr '" 05:57:25 1995

```
1161    Fmt ( scratch, "%s(%f[p0]", max_knock_pump[2]);
1162    SetCtrlVal (panel[3], DATA_MAXPUMP2, scratch);
1163    Fmt ( scratch, "%s(%f[p0]", max_knock_pump[3]);
1164    SetCtrlVal (panel[3], DATA_MAXPUMP3, scratch);
1165    Fmt ( scratch, "%s(%f[p0]", max_knock_pump[4]);
1166    SetCtrlVal (panel[3], DATA_MAXPUMP4, scratch);
1167  }
1168
1169  void temp_read (int k)
1170      /* int k determines if data is held for temp var. during the test. */
1171      /* k = 0 test is not running, do not keep data.                    */
1172      /* k = 1 test is running check data for variance with base temp.   */
1173      /* k = 2 hold temps as base temperatures for variance measurement  */
1174  {
1175    int i, up_dat[4];
1176    double dat1[2], intemp[1], mxtemp[1], ibase, mbase, st_temp;
1177
1178    rs_comm (PORTA,"to\r");              /* request temps from external */
1179    Scan (up_ld,"%s)%4i[x]",up_dat);
1180
1181    for (i=0; i<=1; i++)  {                         /* temp scaling */
1182        dat1[i] = up_dat[i];                    /* water/oil same plot */
1183    }
1184        intemp[0] = up_dat[2];
1185        mxtemp[0] = up_dat[3];
1186
1187    PlotStripChart (panel[3], DATA_INAIR, intemp, 1, 0, 0, 4); /* show temp
      data */
1188     PlotStripChart (panel[1], TEMP_WATER, dat1, 2, 0, 0, 4);
1189     SetCtrlVal (panel[3], DATA_ITEMP, intemp[0]);
1190    if (test_type == 0)   {                     /* if MON show data  */
1191     SetCtrlVal (panel[3], DATA_MTEMP, mxtemp[0]);
1192     PlotStripChart (panel[3], DATA_MXAIR, mxtemp, 1, 0, 0, 4);
1193    }
1194
1195    if (k == 0)   {              /* test is not running check max. & mins */
1196      GetCtrlVal (panel[3], DATA_STTEMP, &st_temp);
1197      if (test_type == 1)   {
1198        if ( intemp[0] > (st_temp + 40.0) ) /*check for correct inlet temp*/
1199        SetCtrlVal (panel[3], DATA_HITEMP, 1); /*led for high inlet temp */
1200        else
1201        SetCtrlVal (panel[3], DATA_HITEMP, 0);
1202
1203        if ( intemp[0] < (st_temp - 40.0) )
1204        SetCtrlVal (panel[3], DATA_LITEMP, 1); /* led for low inlet temp */
1205        else
1206        SetCtrlVal (panel[3], DATA_LITEMP, 0);
1207      }
1208      if (test_type == 0) {                     /* mix check for MON */
1209         if ( mxtemp[0] > 325.0 )
1210           SetCtrlVal (panel[3], DATA_HMTEMP, 1);/*led for high mix temp */
1211         else
1212           SetCtrlVal (panel[3], DATA_HMTEMP, 0);
1213
1214         if ( mxtemp[0] < 285.0 )
1215           SetCtrlVal (panel[3], DATA_LMTEMP, 1);/* led for low mix temp */
1216         else
1217           SetCtrlVal (panel[3], DATA_LMTEMP, 0);
1218
1219         if ( intemp[0] > 105.0 )
```

```
Page 22    LG3M.C  Thu Apr 1' 05:57:25 1995

1220              SetCtrlVal (panel[3], DATA_HITEMP, 1);/*led for high mix temp*/
1221            else
1222              SetCtrlVal (panel[3], DATA_HITEMP, 0);
1223
1224            if ( intemp[0] < 95.0 )
1225              SetCtrlVal (panel[3], DATA_LITEMP, 1);/* led for low inlet temp
     */
1226            else
1227              SetCtrlVal (panel[3], DATA_LITEMP, 0);
1228          }
1229          SetCtrlVal (panel[1], TEMP_OILTEMP, dat1[0]);
1230          SetCtrlVal (panel[1], TEMP_WTEMP, dat1[1]);
1231          SetCtrlAttribute (panel[1], TEMP_OILTEMP, 6, 13);
1232          SetCtrlAttribute (panel[1], TEMP_WTEMP, 6, 11);
1233        }
1234        else if (k == 1)  {         /* test is running, check variation  */
1235          GetCtrlVal (panel[1], TEMP_IBASE, &ibase);
1236          GetCtrlVal (panel[1], TEMP_MBASE, &mbase);
1237          if ( intemp[0] > (ibase + 2.0) )
1238            SetCtrlVal (panel[3], DATA_HITEMP, 1);/* led for high inlet temp */
1239          else
1240            SetCtrlVal (panel[3], DATA_HITEMP, 0);
1241
1242          if ( intemp[0] < (ibase - 2.0) )
1243            SetCtrlVal (panel[3], DATA_LITEMP, 1); /* led for low inlet temp */
1244          else
1245            SetCtrlVal (panel[3], DATA_LITEMP, 0);
1246
1247          if (test_type == 0)    {
1248            if ( mxtemp[0] > (mbase + 2.0) )
1249              SetCtrlVal (panel[3], DATA_HMTEMP, 1);/* led for high mix temp */
1250            else
1251              SetCtrlVal (panel[3], DATA_HMTEMP, 0);
1252
1253            if ( mxtemp[0] < (mbase - 2.0) )
1254              SetCtrlVal (panel[3], DATA_LMTEMP, 1); /* led for low mix temp */
1255            else
1256              SetCtrlVal (panel[3], DATA_LMTEMP, 0);
1257          }
1258        }
1259
1260        else if (k == 2)    {              /* hold base temperature data */
1261          SetCtrlVal ( panel[1], TEMP_IBASE, intemp[0]);
1262          SetCtrlVal ( panel[1], TEMP_MBASE, mxtemp[0]);
1263
1264          if ( dat1[0] < 120.0 || dat1[0] > 150.0) {       /* engine oil */
1265              SetCtrlVal (panel[1], TEMP_OILTEMP, dat1[0]);
1266              SetCtrlVal (panel[1], TEMP_WTEMP, dat1[1]);
1267              SetCtrlAttribute (panel[1], TEMP_OILTEMP, 6, 13);
1268              SetActivePanel (panel[1]);
1269              GetUserEvent(TRUE,&handle,&id);      /* check for user input */
1270              SetCtrlAttribute (panel[1], TEMP_OILTEMP, 6, 7);
1271              HidePanel (panel[1]);
1272              DisplayPanel (panel[3]);
1273              DisplayPanel (panel[4]);
1274              SetActivePanel (panel[4]);
1275          }
1276
1277          if ( dat1[1] < 207.0 || dat1[1] > 214.0) {      /* engine coolant */
1278              SetCtrlVal (panel[1], TEMP_OILTEMP, dat1[0]);
```

```
Page 23    LG3M.C    Thu Apr 17 05:57:25 1995

1279            SetCtrlVal (panel[1], TEMP_WTEMP, dat1[1]);
1280            SetCtrlAttribute (panel[1], TEMP_WTEMP, 6, 11);
1281            SetActivePanel (panel[1]);
1282            GetUserEvent(TRUE,&handle,&id);     /* check for user input */
1283            SetCtrlAttribute (panel[1], TEMP_WTEMP, 6, 7);
1284            HidePanel (panel[1]);
1285            DisplayPanel (panel[3]);
1286            DisplayPanel (panel[4]);
1287            SetActivePanel (panel[4]);
1288        }
1289      }
1290    }                                          /* end of temp_read */
1291
1292    void log_faults (int dec_handle, char *message ) /* log I/O errors to file
        */
1293    {
1294      int file_handle;
1295      char *drive;
1296      drive = "          ";
1297
1298      GetCtrlVal (panel[5],CNFG_NET_DRV, drive);
1299      MakePathname ( drive, "error.log", path);
1300      file_handle = OpenFile ( path, 2, 1, 1);
1301      if ( file_handle < 0) {                  /* check for valid file handle */
1302        MessagePopup ("Could not open file, check network"); /* bad file handl
        e */
1303        drive = "c:\\knock";
1304        MakePathname ( drive, "error.log", path);
1305        file_handle = OpenFile (path, 2, 1, 1);
1306      }
1307      if (dec_handle == 8)
1308        FmtFile ( file_handle, "%s[w10]  %s[w10]  %s[w8] %s[w15]",
1309          DateStr (), TimeStr (), oper, desc1);
1310      else
1311        FmtFile ( file_handle, "%s[w10]  %s[w10]  %s[w8] %s[w15]",
1312          DateStr (), TimeStr (), oper, desc2);
1313      FmtFile ( file_handle, " %s\n", message );
1314      CloseFile (file_handle);
1315    }
1316    void final_data ( int pnll, int mde, double sttd, double rated,
1317    char meth_n[4], int nm_rn, char eng[3], double over)
1318    {
1319      double mean_val, s_dev;
1320      char coct[7], desc[20];
1321      int file, k;
1322
1323      HidePanel (panel[3]);
1324      SetPanelAttribute (panel[12], 0, desc2);
1325      SetPanelAttribute (panel[7], 0, desc1);
1326      SetCtrlVal (pnll, FINAL_DATE1, DateStr());
1327      SetCtrlVal (pnll, FINAL_TIME_1, TimeStr());
1328      DisplayPanel (pnll);
1329      StdDev(mxknk_1, nm_rn, &mean_val, &s_dev);
1330      SetCtrlVal (pnll, FINAL_AVGKNK_1, mean_val);
1331      SetCtrlVal (pnll, FINAL_STDKNK_1, s_dev);
1332      StdDev(mxknk_2, nm_rn, &mean_val, &s_dev);
1333      SetCtrlVal (pnll, FINAL_AVGKNK_2, mean_val);
1334      SetCtrlVal (pnll, FINAL_STDKNK_2, s_dev);
1335      StdDev(mxknk_3, nm_rn, &mean_val, &s_dev);
1336      SetCtrlVal (panel[7], FINAL_AVGKNK_3, mean_val);
```

```
1337        SetCtrlVal (panel[7], FINAL_STDKNK_3, s_dev);
1338        StdDev(mxknk_4, nm_rn, &mean_val, &s_dev);
1339        SetCtrlVal (panel[12], FINAL_AVGKNK_3, mean_val);
1340        SetCtrlVal (panel[12], FINAL_STDKNK_3, s_dev);
1341        StdDev(mxpmp_1, nm_rn, &mean_val, &s_dev);
1342        SetCtrlVal (pnll, FINAL_AVGPMP_1, mean_val);
1343        SetCtrlVal (pnll, FINAL_STDPMP_1, s_dev);
1344        StdDev(mxpmp_2, nm_rn, &mean_val, &s_dev);
1345        SetCtrlVal (pnll, FINAL_AVGPMP_2, mean_val);
1346        SetCtrlVal (pnll, FINAL_STDPMP_2, s_dev);
1347        StdDev(mxpmp_3, nm_rn, &mean_val, &s_dev);
1348        SetCtrlVal (panel[7], FINAL_AVGPMP_3, mean_val);
1349        SetCtrlVal (panel[7], FINAL_STDPMP_3, s_dev);
1350        StdDev(mxpmp_4, nm_rn, &mean_val, &s_dev);
1351        SetCtrlVal (panel[12], FINAL_AVGPMP_3, mean_val);
1352        SetCtrlVal (panel[12], FINAL_STDPMP_3, s_dev);
1353        StdDev(oct_3, nm_rn, &mean_val, &s_dev);
1354        SetCtrlVal (panel[7], FINAL_AVGOCT_3, mean_val);
1355        SetCtrlVal (panel[7], FINAL_STDOCT_3, s_dev);
1356        StdDev(oct_4, nm_rn, &mean_val, &s_dev);
1357        SetCtrlVal (panel[12], FINAL_AVGOCT_3, mean_val);
1358        SetCtrlVal (panel[12], FINAL_STDOCT_3, s_dev);
1359        SetCtrlVal (pnll, FINAL_OPER_1, oper);
1360        SetCtrlVal (pnll, FINAL_TOL_1, sttd);
1361        SetCtrlVal (pnll, FINAL_RATE_1, rated);
1362        SetCtrlVal (pnll, FINAL_METH_1, meth_n);
1363        SetCtrlVal (pnll, FINAL_ENG_1, eng);
1364        SetCtrlVal (pnll, FINAL_OH_1, over);
1365        GetCtrlVal (panel[3], DATA_DESC3, desc);
1366        SetCtrlVal (panel[7], FINAL_DESC_3, desc);
1367        GetCtrlVal (panel[3], DATA_DESC4, desc);
1368        SetCtrlVal (panel[12], FINAL_DESC_3, desc);
1369
1370        if (mde == 1)  {
1371          OutputPanel (-1,"", 0, pnll);
1372          return;
1373        }
1374        while (TRUE)  {
1375         GetUserEvent (TRUE, &handle, &id);
1376          switch (id)     {
1377           case FINAL_PRINT_1:
1378             OutputPanel (-1,"", 0, pnll);
1379             break;
1380          case FINAL_NETWORK_1:
1381            error = ConfirmPopup ("Is the average shown correct?");
1382            if (error == 0)     {
1383              PromptPopup ("Enter the corrected octane number", coct, 5);
1384              log_faults (pnll," Reported edited octane ");
1385              Fmt (&mean_val, "%f(%s", coct);
1386              SetCtrlVal (pnll, FINAL_AVGOCT_3, mean_val);
1387            }
1388            break;
1389          case FINAL_RETR_1:
1390             HidePanel (pnll);
1391             DisplayPanel (panel[3]);
1392             return;
1393             break;
1394        }
1395     }
1396  }
```

Page 25    LG3M.C  Thu Apr 1  05:57:25 1995

```
1397
1398  void data_reset(int j)
1399  {
1400     Clear1D (mxknk_1, 10);
1401     Clear1D (mxknk_2, 10);
1402     Clear1D (mxpmp_1, 10);
1403     Clear1D (mxpmp_2, 10);
1404
1405     if (j == 1)  {
1406        Clear1D (mxknk_3, 10);
1407        Clear1D (mxpmp_3, 10);
1408        Clear1D (oct_3, 10);
1409     }
1410     if (j == 2) {
1411        Clear1D (mxknk_4, 10);
1412        Clear1D (mxpmp_4, 10);
1413        Clear1D (oct_4, 10);
1414     }
1415  }
1416
1417  void help_read (int pnl)
1418  {
1419     int file;
1420     char file_1[25], file_z[13], d_buf[301];
1421
1422     while (1)    {
1423      DefaultCtrl (pnl, HELP_INFO);
1424      GetCtrlVal (pnl, HELP_INDEX, file_1);
1425      CopyString (file_z, 0, file_1, 0, 8);
1426      Fmt (file_z, "%s[a](.hlp)");
1427      MakePathname ("c:\\keas\\help", file_z, path);
1428      error = OpenFile (path, 1,2,1);
1429      ScanFile (error, "%s[w0])%s[t-]", d_buf);
1430      CloseFile (error);
1431      SetCtrlVal (pnl, HELP_INFO, d_buf);
1432      GetPopupEvent ( TRUE, &id);
1433         if (id == 1)   {
1434        DefaultPanel (pnl);
1435        return;
1436         }
1437     }
1438  }
1439
1440  void err_routine (char* function, int erro)
1441  {
1442      char tmpor[40];
1443      Fmt (tmpor, "%s(%s error = %i", function, erro);
1444      MessagePopup (tmpor);
1445      exit (-99);
1446  }
1447
1448  void head_set (void)
1449  {
1450  double hd_set_val;
1451  int head_loc;
1452
1453      GetCtrlVal (panel[3], DATA_OCTANE1, &octane[1]);
1454      GetCtrlVal (panel[3], DATA_OCTANE2, &octane[2]);
1455      if (octane[1] > octane[2])
1456          octane[0] = octane[1];
```

```
Page 26    LG3M.C  Thu Apr   05:57:25 1995

1457            else
1458                octane[0] = octane[2];
1459        if (octane[0] < 120.3) {
1460         if (test_type == 1) {                         /* RON head settings */
1461            if (octane[0] <= 79.9)
1462                hd_set_val = 153.96+(6.7734*octane[0])-(0.073094*pow(octane[0], 2)
        )+
1463                (0.00073855*pow (octane[0], 3));
1464            else if (octane[0] >= 80.0 && octane[0] <= 99.9)
1465                hd_set_val = -7239.9+(270.90*octane[0])-(3.2262*pow(octane[0], 2))
        +
1466                (0.013328*pow(octane[0], 3));
1467            else if (octane[0] >= 100.0 && octane[0] <= 109.9)
1468                hd_set_val = -28869.0+(683.47*octane[0])-(5.085*pow(octane[0], 2))
        +
1469                (0.012291*pow(octane[0], 3));
1470            else if (octane[0] >= 110.0)
1471                hd_set_val = -5189.8+(165.5*octane[0])-(1.5473*pow(octane[0], 2))+
1472                (0.0051487*pow(octane[0], 3));
1473         }
1474         if (test_type == 0)  {                        /* MON head settings 9/16"*/
1475            if (octane[0] <= 79.9)
1476                hd_set_val = -260.43+(18.048*octane[0])-(0.26852*pow(octane[0], 2)
        )+
1477                (2.1317e-3*pow(octane[0], 3));
1478            else if (octane[0] >= 80.0 && octane[0] <= 100.0)
1479                hd_set_val = 7601.6-(264.79*octane[0])+(3.1191*pow(octane[0], 2))-
1480                (1.1368e-2*pow(octane[0], 3));
1481            else if (octane[0] >= 100.1 && octane[0] <= 103.1)
1482                hd_set_val = 1.6557e+5-(4899.8*octane[0])+(48.485*pow(octane[0], 2
        ))-
1483                (0.15949*pow(octane[0], 3));
1484            else if (octane[0] >= 103.2)
1485                hd_set_val = -1.6536e+4+(444.73*octane[0])-(3.8042*pow(octane[0],
        2))+
1486                (1.1048e-2*pow(octane[0], 3));
1487         }
1488         head_loc = round (hd_set_val);
1489
1490         if (baro <= 29.9)
1491            SetCtrlVal (panel[3], DATA_HEAD1, head_loc+hd_cor);
1492         else
1493            SetCtrlVal (panel[3], DATA_HEAD1, head_loc-hd_cor);
1494         SetCtrlVal (panel[3], DATA_HEAD, head_loc);
1495        }
1496 }
1497
1498 void gas_valve (int pos)
1499 {
1500  char serial_dt[4];
1501  int z;
1502
1503  Fmt (serial_dt, "%s<i%i\r", pos);        /* i command for gas in Zworld */
1504  rs_comm (PORTA,serial_dt);
1505  Scan (up_ld, "%s>%i[w1]", &z);
1506  SetCtrlVal(panel[3], DATA_NGASST, z);
1507  SetCtrlVal (panel[3], DATA_NGAS_SW, z);
1508   if (z == 1)
1509      setpump (0.0);
1510   else
```

Page 27    LG3M.C    Thu Apr 1? 05:57:25 1995

```
1511        setpump (ref_pump_set);
1512    return;
1513  }
1514
1515  void drain_valve (char snd_dat[2], int pos)
1516  {
1517    char serial_dat1[5];
1518
1519    Fmt (serial_dat1, "%s(%s%i\r", snd_dat, pos);
1520    rs_comm (PORTA,serial_dat1);
1521    return;
1522  }
1523
1524  void rs_comm (int port, char down_load[9])
1525  {
1526    char up_load[8], dmp[4];
1527    int i,k, addr, intr;
1528    double est_pumpset;
1529
1530    i=0;                                            /* counter set to zero */
1531
1532    if (port == PORTB)  {
1533       addr = 0x2E8;
1534       intr = 5;
1535    }
1536    else  {
1537       addr = 0;
1538       intr = 0;
1539    }
1540    OpenComConfig (port, 9600, 0, 8, 1, 64, 64, addr, intr);
1541    if ( rs232err != 0 )
1542      err_routine ( "Com Port ", rs232err );
1543    k=StringLength (down_load);
1544    while (i<3)          {           /* loop to ensure data trans & receive */
1545      if (port == PORTB)
1546        error= ComWrt(port, "\x1b", 1);
1547      FlushInQ (port);                              /* clear port buffers */
1548      FlushOutQ (port);
1549      FillBytes (up_ld, 0, 25, 0);           /* clear data receive buffer */
1550      FillBytes (up_load, 0, 8, 0);
1551      SetComTime (port, 2.0);
1552      error = ComWrt (port, down_load, k);
1553        if (error != k)
1554        err_routine ("RS232 communication", rs232err);
1555      delay(0.5);
1556      ComRd (port, up_load, k);
1557      error = CompareBytes (down_load, 0, up_load, 0, k-1, 1);
1558      if (error == 0)  {
1559        if (port == PORTA)  {
1560         if (FindPattern(down_load, 0, 2, "9", 0, 0) == 1)
1561          SetComTime (port, 11.0);
1562          while (!ComRdTerm(port, up_ld, 24, 13) && rs232err == 0) {}
1563        }
1564        else if (port == PORTB)  {
1565          Scan (down_load, "%s[i2t10])%f[x]", &est_pumpset);
1566          delay(fabs((up_pump-est_pumpset)*0.0004));    /* variable delay */
1567          ComWrt(port, "Kz\n", 3);                  /* based on pump change */
1568          delay(0.3);
1569          ComRd(port, dmp, 3);
1570          while (!ComRdTerm(port, up_ld, 24, 10) && rs232err == 0) {}
```

```
Page 28    LG3M.C  Thu Apr 1  05:57:25 1995

1571        }
1572      }
1573      if (rs232err == 0 && error == 0) {        /* return if commun. ok */
1574        CloseCom (port);
1575        return;
1576      }
1577      i++;
1578    }                                           /* increment */
1579    if (port == PORTB)
1580      error= ComWrt(port, "\x1b", 1);
1581    CloseCom (port);
1582    return;
1583  }
1584
1585  void wait (double time_dly)
1586  {
1587  double systm_time_1;
1588  systm_time_1 = timer();
1589
1590    while (timer() < systm_time_1 + time_dly)  {
1591      GetUserEvent(FALSE, &handle, &id);
1592      abort_check(&handle, &id);
1593      if (abort_flag == TRUE)
1594        return;
1595    }
1596  return;
1597  }
```

That which is claimed:

1. A computer implemented method for determining the octane number of a test fuel comprising the steps of:

(a) inputting data characterizing a first reference fuel and a second reference fuel into a computer;

(b) sending a first signal from said computer to a selector valve operationally connected to said computer so that upon receiving said first signal said selector valve changes to a first position in which said first reference fuel is introduced to a variable flow pump in fluid flow communication with an engine so that fluid introduced to said variable flow pump is introduced to said engine at a flow rate wherein said variable flow pump is operationally connected to said computer such that said computer can send a flow signal to said variable flow pump and thereby change said flow rate;

(c) determining the maximum knock level for said first reference fuel;

(d) sending a second signal from said computer to said selector valve so that upon receiving said second signal said selector valve changes to a second position in which said second reference fuel is introduced to said variable flow pump;

(e) determining the maximum knock level for said second reference fuel;

(f) sending a third signal from said computer to said selector valve so that upon receiving said third signal said selector valve changes to a third position in which a test fuel is introduced to said variable flow pump;

(g) determining the maximum knock level of said test fuel; and (h) calculating a test fuel octane number for said test fuel by linear interpolation using said test fuel's maximum knock level, said first reference fuel's maximum knock level and said second reference fuel's maximum knock level; and (i) displaying said test fuel octane number;

wherein said determining of each maximum knock level comprises:

sending a series of flow signals to change said fuel flow rate so that each fuel is delivered for combustion within said engine at a plurality of flow rates starting at a predetermined initial flow rate and changing the flow rate towards a flow rate that is likely to produce the maximum knock level;

sending, at each flow rate, a pressure signal from said engine to said computer wherein said pressure signal is representative of the rate of change of the cylinder pressure in said engine during the combustion of fuel within said engine;

acquiring at each flow rate a plurality of data arrays in response to said pressure signal wherein said plurality of data arrays contain data centered about the combustion part of the cycle of said engine;

calculating an average knock intensity from said plurality of data arrays for each flow rate;

comparing said average knock intensity for each flow rate, other than said initial flow rate, to said average knock intensity obtained for the previous flow rates to determine if a maximum average knock intensity for said plurality of flow rates has been found;

calculating thereafter a polynomial expression for the distribution of said average knock intensity for said plurality of flow rates;

calculating the maximum knock intensity value of said polynomial expression and obtaining a corresponding flow rate for the fuel;

adjusting said flow rate to said corresponding flow rate;

acquiring said plurality of data arrays for said corresponding flow rate; and calculating a maximum knock level from said plurality of data arrays for said corresponding flow rate.

2. A method according to claim 1 further comprising:

calculating a new initial flow rate for said test fuel based on said maximum knock level for said test fuel, repeating steps (g) and (h) to obtain a second test fuel octane number for said test fuel wherein said second initial pump setting is used in place of said initial pump setting, and calculating a second octane number for said test fuel.

3. A method according to claim 1 wherein one of said reference fuels has an octane number greater than said test fuel octane number and the other of said reference fuels has an octane number less than said test fuel octane number.

4. An apparatus comprising:

a first fuel bowl for containing a first reference fuel having a first known octane number;

a second fuel bowl for containing a second reference fuel having a second known octane number;

a third fuel bowl for containing a first test fuel having an unknown octane number;

an engine having a fuel inlet;

a variable flow pump for delivering fuel to said engine where in the fuel flow rate at which fuel is delivered by said variable flow pump can be changed;

a selector valve having a first inlet in fluid flow communication with said first fuel bowl for receiving said first reference fuel, a second inlet in fluid flow communication with said second fuel bowl for receiving said second reference fuel, a third inlet in fluid flow communication with said third fuel bowl for receiving said first test fuel and an outlet port in fluid flow communication with said first port when said selector valve is in a first position, in fluid flow communication with said second port when said selector valve is in a second position and in fluid flow communication with said third port when said selector valve is in a third position wherein said outlet port is in fluid flow communication with said variable flow pump such that fuel is delivered from said outlet port to said variable flow pump;

means for establishing a pressure signal representative of the rate of change of the cylinder pressure in said engine during the combustion of fuel within said engine;

a computer operationally connected to said means for establishing a pressure signal such that in response to said pressure signal said computer acquires a plurality of data arrays centered about the combustion part of the cycle of said engine, operationally connected to said variable flow pump such that said computer can send a flow signal to said variable flow pump and thereby change the fuel flow rate of fuel being delivered by said variable flow pump, and operationally connected to said selector valve such that said computer can change the position of said selector valve, wherein said computer is programmed to change the position of said selector valve to said first position, determine the maximum knock level for said first reference fuel, change the position of said selector valve to said second position, determine the maximum knock level for the second reference fuel, change the position of said selector valve to said third position, determine the maximum knock level of said test fuel, calculate a test fuel octane number for said test fuel by linear interpolation using said test fuel's maximum knock level, said first reference fuel's maximum knock level and said second reference fuel's maximum knock level, and display said test fuel octane number, wherein said determination of the maximum knock level comprises:

sending a series of flow signals to change the fuel flow rate so that each fuel is delivered for combustion within said engine at a plurality of flow rates starting at a predetermined initial flow rate and changing the flow rate towards a flow rate that is likely to produce said maximum knock level;

acquiring at each flow rate said plurality of data arrays;

calculating an average knock intensity for each flow rate from said plurality of data arrays;

comparing said average knock intensity for each flow rate, other than said initial flow rate, to said average knock intensity obtained for the previous flow rates to determine if a maximum average knock intensity for said plurality of flow rates has been found;

calculating a polynomial expression for the distribution of said average knock intensity for said plurality of flow rates;

calculating the maximum knock intensity value of said polynomial expression and obtaining a corresponding flow rate for the fuel;

adjusting said flow rate to said corresponding flow rate;

acquiring said plurality of data arrays for said corresponding flow rate; and calculating a maximum knock level from said plurality of data arrays for said corresponding flow rate.

5. An apparatus according to claim 4 further comprising an air intake means for mixing fuel and air prior to introduction of said fuel into said engine wherein said air intake means uses a venturi tube to mix said air and fuel and said air enters said venturi tube at a constant rate such that said fuel flow rate determines the air to fuel ratio in the resulting air/fuel mixture.

* * * * *